(12) United States Patent
Axelrod

(10) Patent No.: US 10,485,444 B2
(45) Date of Patent: Nov. 26, 2019

(54) SYSTEMS AND METHODS FOR PROCESSING ELECTROMYOGRAPHIC SIGNALS OF THE GASTROINTESTINAL TRACT

(71) Applicant: G-Tech Medical, Inc., Mountain View, CA (US)

(72) Inventor: Steve Axelrod, Los Altos, CA (US)

(73) Assignee: G-Tech Medical, Inc., Mountain View, CA (US)

( * ) Notice: Subject to any disclaimer, the term of this patent is extended or adjusted under 35 U.S.C. 154(b) by 221 days.

(21) Appl. No.: 15/518,929

(22) PCT Filed: Oct. 19, 2015

(86) PCT No.: PCT/US2015/056282
§ 371 (c)(1),
(2) Date: Apr. 13, 2017

(87) PCT Pub. No.: WO2016/061589
PCT Pub. Date: Apr. 21, 2016

(65) Prior Publication Data
US 2017/0231521 A1 Aug. 17, 2017

Related U.S. Application Data

(60) Provisional application No. 62/065,235, filed on Oct. 17, 2014, provisional application No. 62/065,216, filed on Oct. 17, 2014, provisional application No. 62/065,226, filed on Oct. 17, 2014.

(51) Int. Cl.
*A61B 5/04* (2006.01)
*A61B 5/0488* (2006.01)
*A61B 5/00* (2006.01)

(52) U.S. Cl.
CPC ...... *A61B 5/04884* (2013.01); *A61B 5/04017* (2013.01); *A61B 5/6833* (2013.01); *A61B 5/7203* (2013.01)

(58) Field of Classification Search
CPC .............. A61B 5/04884; A61B 5/7203; A61B 5/04017; A61B 5/6833
See application file for complete search history.

(56) References Cited

U.S. PATENT DOCUMENTS 5,704,368 A  1/1998  Asano et al.
5,795,304 A  8/1998  Sun et al.
(Continued)

FOREIGN PATENT DOCUMENTS

| WO | 199610358 A1 | 4/1996 |
|----|--------------|--------|
| WO | 2010068818 A2 | 6/2010 |
| WO | 2010121038 A1 | 10/2010 |
| WO | 2012060874 A2 | 5/2012 |

OTHER PUBLICATIONS

Haddab, S. et al., "Microcontroller-Based System for Electrogastrography Monitoring Through Wireless Transmission," Measurement Science Review, 2009, p. 122-126, vol. 9, No. 5.
(Continued)

*Primary Examiner* — Christian Jang
(74) *Attorney, Agent, or Firm* — Aurora Consulting LLC; Ashley Sloat

(57) ABSTRACT

Embodiments of a method for removal and replacement of artifacts in electrophysiological data from muscular activity in the a gastrointestinal tract of a patient are disclosed. The approach includes setting an artifact identification threshold based on the parameters of the data, assessing the full extent of the artifact in time, and replacing the values with ones that are neutral in the time series and minimizing the effect on a power spectrum of the data. More particularly, the method includes steps of identifying artifacts within the raw time series data, eliminating the identified artifacts, and replacing the artifacts with any of interpolated points or constant value points to create a clean time series data set representing valid gastrointestinal tract EMG signals.

22 Claims, 41 Drawing Sheets

(56) References Cited

U.S. PATENT DOCUMENTS

| | | | |
|---|---|---|---|
| 5,857,980 | A | 1/1999 | Wilson |
| 6,351,665 | B1 | 2/2002 | Koch |
| 7,160,254 | B2 | 1/2007 | Noar |
| 7,593,768 | B1 | 9/2009 | Vasilev et al. |
| 9,943,264 | B2 * | 4/2018 | Axelrod ............... A61B 5/0492 |
| 9,955,914 | B2 | 5/2018 | Dunki-Jacobs et al. |
| 2003/0069714 | A1 | 4/2003 | Wigley et al. |
| 2004/0260164 | A1 | 12/2004 | Kilcoyne et al. |
| 2005/0209709 | A1 * | 9/2005 | Bradshaw ........ G06Q 10/06398 700/2 |
| 2005/0215917 | A1 | 9/2005 | Noar |
| 2006/0058606 | A1 * | 3/2006 | Davis ....................... A61B 5/05 600/407 |
| 2006/0107954 | A1 * | 5/2006 | Katz ..................... A61B 5/0205 128/204.23 |
| 2006/0149541 | A1 * | 7/2006 | Jaklitsch ................. G10L 25/78 704/226 |
| 2006/0258927 | A1 * | 11/2006 | Edgar, Jr. ........... A61B 5/14551 600/336 |
| 2007/0167859 | A1 * | 7/2007 | Finneran ............... A61B 5/0492 600/546 |
| 2007/0225576 | A1 | 9/2007 | Brown et al. |
| 2007/0287931 | A1 | 12/2007 | Dilorenz |
| 2008/0154110 | A1 | 6/2008 | Burnes et al. |
| 2009/0318783 | A1 | 12/2009 | Rohde et al. |
| 2010/0172839 | A1 | 7/2010 | Walker |
| 2010/0228105 | A1 | 9/2010 | Policker et al. |
| 2010/0292606 | A1 * | 11/2010 | Prakash ............... A61B 5/0488 600/554 |
| 2013/0046150 | A1 | 2/2013 | Devanaboyina |
| 2014/0226158 | A1 * | 8/2014 | Trainer .................... G02B 6/32 356/336 |
| 2016/0121111 | A1 | 5/2016 | Levine et al. |

OTHER PUBLICATIONS

Chen, J. D. Z. et al., "Detection of gastric slow wave propagation from the cutaneous electrogastrogram," Am J Physiol, 1999, p. G424-G430 vol. 277.

Kim, D. W. et al., "Usefulness of a Developed Four-Channel EGG System with running spectrum analysis," Yonsei Medical Journal, 2000, p. 230-236, vol. 41. No. 2.

Garcia-Casado, J. et al., "Noninvasive Measurement and Analysis of Intestinal Myoelectrical Activity Using Surface Electrodes," IEEE Transactions on Biomedical Engineering, Jun. 2005, p. 983-991, vol. 52, No. 6.

Chen, J. D. Z. et al., "Measurement of Electrical Activity of the Human Small Intestine Using Surface Electrodes," IEEE Transactions on Biomedical Engineering, Jun. 1993, p. 598-602, vol. 40, No. 6.

Lammers, W. J. E. P et al., "Orgin and propagation of the slow wave in the canine stomach: the outlines of a gastric conduction system," Am J Physiol Gastrointest Liver Physiol, 2009, p. G1200-G1210, vol. 296.

Leahy, A. et al., "Abnormalities of the Electrogastrogram in Functional Gastrointestinal Disorders," American Journal of Gastroenterology, 1999, p. 1023-1028, vol. 94, No. 4.

Myers, T. J. et al., "Human Surface Electrogastrograms: AC and DC measurements," Annals of Biomedical Engineering, 1984, p. 319-333, vol. 12.

Wang, Z. S. et al., "Detection of gastric slow wave uncoupling from multi-channel electrogastrogram: validations and applications," Neurogastroenterol Motil, 2003, p. 457-465, vol. 15.

Written Opinion issued on PCT Application Serial No. PCT/US2011/01848 by ISA/US dated May 21, 2012, p. 1-5.

International Search Report issued on PCT Application Serial No. PCT/US2011/01848 by ISA/US dated May 21, 2012, p. 1-4.

Madsen et al., "Listening to Bowel Sounds: An Evidence-Based Practice Project," Dec. 2005, AJN, vol. 105, No. 12, p. 40-48.

"Home—ePatch," Delta Danish Electronics, Light & Acoustics, [Accessed Jul. 1, 2016] <http://epatch.madebydelta.com>.

Haahr, R. et al., "A wearable 'electronic patch' for wireless continuous monitoring of chronically diseased patients," 5th International Summer School and Symposium on Medical Devices and Biosensors, 2008, p. 66-70.

Sanders, K. M. et al., "Interstitial cells of Cajal as pacemakers in the gastrointestinal tract," Annu Rev Physiol, 2006, p. 307-343, vol. 68.

International Search Report and Written Opinion issued for PCT/US2015/056282 by ISA/US dated Jan. 20, 2016 (9 pages).

* cited by examiner

SYSTEMS AND METHODS FOR PROCESSING ELECTROMYOGRAPHIC SIGNALS OF THE GASTROINTESTINAL TRACT

CROSS-REFERENCE TO RELATED APPLICATIONS

This application is the U.S. National Stage Application for PCT Application Ser. No. PCT/US2015/056282, filed Oct. 19, 2015, which claims the benefit of: U.S. Provisional Application No. 62/065,216, titled "Method for removing artifacts from time series data representing electromyographic activity of the gastrointestinal tract," filed Oct. 17, 2014, which is herein incorporated by reference in its entirely; U.S. Provisional Application No. 62/065,226, titled "Method for normalization across multiple sets of time series data representing electromyographic activity of the gastrointestinal tract," filed Oct. 17, 2014, which is herein incorporated by reference in its entirety; and U.S. Provisional Application No. 62/065,235, titled "Method for identifying and measuring characteristics of peaks in the frequency spectrum of data representing electromyographic activity of the gastrointestinal tract," filed Oct. 17, 2014, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to systems and methods for profiling electrical activity within the smooth muscle of the gastrointestinal tract, and more particularly to systems and methods for processing electronic time series recordings from electromyographic activity of the gastrointestinal tract used for diagnosing gastrointestinal motility disorders.

BACKGROUND

Methods and systems for obtaining electromyography (EMG) data from the gastrointestinal tract, of patients, particularly patients who appear to suffer from disorders related to gastrointestinal motility, are known in the prior art and practiced by specialists in the art. Such systems and methods typically are used in a procedure that occurs in a clinical setting, within a time frame of several hours and wherein the patient needs to be substantially in repose. Further, the testing procedure usually asks the patient to adhere to a preliminary schedule of eating, and of eating a standardized meal.

These constraints, however practical and appropriate, nevertheless can limit the scope of data derived from such studies. The data are limited in time frame, that is, a study is only feasible for several hours, during which a patient can tolerate or comply with the constraint on normal physical activity. This limitation can be understood from the perspective that gastrointestinal activity occurs in the context of a daily cycle, and that daily cycle occurs in the context of activities of daily living. Gastrointestinal pain or discomfort also can be cyclical or intermittent throughout the day, of over the course of several days. Such intermittency may or may not be clearly tied to activities associated with the gastrointestinal tract specifically or the more general and varied activities of daily living. Accordingly, signals and patterns of interest may not present themselves in the limited observational window of the clinical test; thus, the diagnostic value of gastrointestinal activity data derived from tests that include such constraints is limited.

Further, such a gastrointestinal EMG study, as currently practiced, is expensive in that it occupies space in the clinic, and it occupies the time of the healthcare provider who is administering the testing procedure. As a consequence of the cost that limits the prevalence of such testing, the testing is generally applied to severe cases of gastrointestinal distress or to cases that are otherwise difficult to diagnose. And further still, the limited use of such testing limits the accumulation of data as a whole; accordingly, it is not possible to acquire population-wide data, which would advance understanding of the relationship between dysfunctional gastrointestinal electrical activity and gastrointestinal disorders.

There is a need in the medical marketplace for systems and methods that are more affordable, and which provide, a more comprehensive view of gastrointestinal activity throughout a day or for longer periods, and which can monitor such activity while the patient is free to conduct the normal activities of daily living.

SUMMARY

Systems and methods are provided herein which address one or more of the shortcomings of existing EMG monitoring systems and methods. In particular, systems and methods are provided herein which allow for non-clinical acquisition and processing of EMG signals from the smooth muscles of the gastrointestinal tract (GI). Systems and methods provided herein are configured to wirelessly acquire EMG signals and process the signals to generate meaningful data of gastrointestinal activity and motility for diagnostic and monitoring purposes.

One aspect of the disclosure is directed to a method of producing an accurate and reliable graphical representation of EMG signals generated by the GI tract of a patient. In various embodiments, the method includes acquiring a raw time series data set of signals from a skin-surface mounted electrode patch. The patch of various embodiments is positioned on the surface of a patient's skin over the abdominal region. The method further includes: extracting valid gastrointestinal tract EMG data from the raw time series data set, normalizing the amplitude of the extracted gastrointestinal EMG data set, and characterizing parameters of peaks in the frequency spectrum of the normalized gastrointestinal EMG data set. The method may further include generating an output of the processed data for display. Another aspect of the disclosure is directed to devices and systems configured to perform the various methods described herein. While wireless monitoring of EMG signals has been previously proposed, existing systems fail to output readable and reliable data of clinical value. Embodiments provided herein are directed to systems and methods of extracting, cleaning, and processing voltage signals acquired from the abdominal region to generate a clinically valuable output for GI diagnostics and monitoring.

Embodiments of the present disclosure include methods for extracting valid gastrointestinal tract EMG data from a raw time series data set acquired from a skin-surface mounted electrode patch. These method embodiments include identifying artifacts within the raw time series data, such identifiable artifacts including a set of data points nominally centered on a point of largest excursion (positive or negative) from average value of zero-crossing, and extending toward the average or zero-crossing. Embodiments may further include eliminating the identified artifacts by tracking them down to any of a zero-crossing or a midpoint-crossing point, on either side of a high amplitude artifact; and replacing the artifacts with any of interpolated points or constant value points that span a gap across the eliminated artifacts. These steps create a clean time series data set that represents valid gastrointestinal tract EMG signals.

In some embodiments of the method, identifying artifacts is based on the standard deviation of a set of points in the data set. Artifacts are typically identified by having at least one data point being beyond a particular or predetermined limit, such as five standard deviations. The set of points may be the entire data set, or any of various subsets such as a local set of points or a standard set of points. Use of such a local subset could be employed in lieu of the entire set, as for example, in order to overcome the effect of relatively gradual drift in the full data set.

In some embodiments of the method, identifying artifacts is based on a percentile ranking of a set of points where the artifact is identified is a structure having at least one data point in art extreme percentile. For example, in a bipolar data set, any point below the 2nd percentile or above the 98th percentile might be indicative of an artifact. Alternatively, taking absolute values of all points could be used to identify artifacts solely on the basis of being above a chosen or predetermined percentile rank.

In some embodiments of the method, identifying artifacts includes filtering the raw data to remove low frequencies or high frequencies. In some embodiments of the method, identifying artifacts includes offsetting data amplitude by an averaged amplitude value for the entire data set, thereby creating a data set with an average value of zero.

In some embodiments of the method, identifying artifacts includes tracking data points to the nearest zero-crossing or midpoint-crossing, the individual point nearest to zero/midpoint is selected on either side, and replacement points are interpolated between the two points so determined.

In some embodiments of the method, identifying artifacts includes tracking to the nearest zero-crossing or midpoint-crossing, and all replacement points are set to zero or to the midpoint value as appropriate.

In some embodiments of the method, replacing artifacts includes smoothing of values on either or both sides of the gap between eliminated artifacts minimize spectral effects from an abrupt edge transition.

In some embodiments of the method, replacing the artifacts further includes recording any of the number of replaced data points or the amount of elapsed time associated with them to allow any further data processing to compensate for the absence of data. For example, if 10% of the data is replaced, later processing that determines parameters that sum up activity or energy or any other parameter over time will be able to be scaled appropriately to make up for the loss of data.

In some embodiments of the method, identifying artifacts includes using a predetermined threshold criterion. For example, a predetermined threshold of 5 standard deviations or above the 98th percentile could be used. In some particular embodiments, using a predetermined threshold criterion is applied in a repetitive or iterative manner. The standard deviation changes after the artifacts are removed in each iterative step, redoing the procedure using the same threshold in standard deviation measures, until the result converges and no points lie outside the number of standard deviations initially specified.

In some embodiments of the method identifying artifacts includes using an adaptive threshold criterion, such adaptive threshold criterion based on statistical measures complementary to the one being used for the threshold. For example after artifacts are removed, the data set may be examined to determine if the remaining points form or approximate a normal distribution or one with higher "tails". In the latter case, for example, the threshold in standard deviations may be lowered and the cleanup procedure redone to reduce the mils and better approximate a normal distribution.

In some embodiments of the method, identifying artifacts includes using characteristics of data shape that have been previously identified as artifactual. In preparing for being able to recognize artifacts, it can by useful to intentionally induce artifacts in test runs. In this manner a library of data shapes can be created that are known to be artifacts, and such known artifact shapes can be used as references for judging whether shapes that appear in test data are artifacts.

By way of example of data shapes that can be suspected of being artifactual, the data shape may include a rapid initial excursion (rise or fall depending on sign) followed by an approximately exponential decay as would be expected from recovery of an electronic circuit that had been overloaded. By way of another example, the shape may include a rapid initial excursion (rise or fall depending on sign) followed by an approximately exponential decay with subsequent ringing as is seen in electronic circuitry recovering from an overload that is under-damped.

In some embodiments of the method, identifying artifacts includes examining raw data sets from multiple channels. Multiple channels may be advantageously examined to provide additional information that allows a determination as to whether a particular time series event pattern is an artifact or part of the valid gastrointestinal tract data. By way of example, when a time series event in raw data coincidentally occurs on a plurality of channels, such coincidence occurrence may be suspected of being an artifact. Valid gastrointestinal tract signals, however, can and do occur on multiple channels, so other criteria may be useful in making artifact determinations. For example, the pattern of amplitudes across channels can be informative. If amplitudes drop off gradually in all directions, the apparent signal is likely to be physiologically valid, but if it is the same or nearly the same across a group of channels its likely due to an electronic glitch or motion glitch.

In some embodiments of the method, identifying artifacts includes recognizing artifacts that have the characteristics of an analog-to-digital conversion (ADC) error (e.g., high amplitude and confined to one or at most a few consecutive points) and may be replaced by data points interpolated between the unaffected points on either side of the ADC error. In particular embodiments, the method may include applying digital filtering after eliminating the ADC error(s).

In some embodiments of the method, identifying artifacts includes evaluating the power spectrum from all or a section of the full data set and concluding that a particular region of the time series data is heavily burdened by artifacts based on the shape of the resulting spectrum. By way of example, if a region of the time series has a spectrum that is, overall, of higher intensity than the preceding and succeeding time periods over the entire region of interest in frequency, and yet shows little or no structure comprised of peaks, but rather has the smooth characteristics such as are commonly referred to as "white noise" or "pink noise", then it is likely that the time region is corrupted by artifacts and should be eliminated from the analysis.

In some embodiments, the method recited above further includes segregating the raw time series data set into sub-regions, the method steps then being applied to each sub-region independently. The application of the above-described method steps within each sub-region can be applied to identify the existence of smaller or larger real signal levels in each sub-region.

In an alternative method embodiment, a modified time series data set is created to aid in the processing of the raw time series data set. Accordingly, a method of extracting valid gastrointestinal tract EMG data from a raw time series data set acquired from a skin-surface mounted electrode patch may include modifying the raw time series data set to create a modified time series data set. The method embodiment then includes identifying artifacts within the modified time series data, the artifacts including a set of data points nominally centered on the point of largest excursion from average value of zero-crossing and extending toward the average or zero-crossing; and eliminating the artifacts identified in the modified time series data from the raw time series data by tracking them down to any of a zero-crossing or a midpoint-crossing point on either side of a high amplitude artifact. The method embodiment then concludes by replacing the artifacts in the raw time series data with any of interpolated points or constant value points that span a gap across the eliminated artifacts to create a clean time series data set comprising valid gastrointestinal tract EMG signals. By way of example, the identification of artifacts can be done with a set filtered to remove drift, but the cleanup done on the original set, using the same point in the sequence as found in the modified data set as the starting point for the algorithm that tracks it to its zero-point or midpoint crossing.

Embodiments of a method for normalizing the amplitude of a gastrointestinal EMG voltage data set acquired from the wireless electrode patch are provided herein. These embodiments make use of data from a standard patient, presumed to be healthy, in the analysis of data from a patient under evaluation for possible gastrointestinal disease or condition.

Accordingly, these method embodiments include identifying a quiet section within a power spectrum of an EMG voltage data set from a standard subject to be used as a normalization reference, the quiet section including one or more voltage ranges, and being free of any apparent valid gastrointestinal tract signals or any apparent artifacts or aberrant data patters. Method embodiments further include calculating the summed energy contained in the quiet section, and based on the summed energy of the quiet section, determining a data normalization value within the normalization range by comparing to the summed energy over the same range(s) in a reference spectrum. Method embodiments further include applying the data normalization value as a scaling factor to the acquired gastrointestinal data set of interest from the patient being evaluated set to mitigate patient-to-patient variation in signal transmission efficiency due to patient variability in amount of tissue and tissue conductivity and/or due to variability in quality of electrode coupling to the skin surface.

As noted above, the standard subject whose data are being used for the normalization reference is presumptively free of any gastrointestinal disease or condition. Standard subject data may be acquired from multiple standard patients, and combined so as to create a statistically more robust standard patient data set.

In practicing embodiments of the method, the normalization value to be applied to the acquired gastrointestinal data from a patient being evaluated is acquired from a particular location on the abdomen of the standard subject, and wherein the data set from the patient being evaluated is acquired from the same particular location as that of the standard subject.

In some embodiments of the method, the normalization value to be applied to the acquired gastrointestinal data from the patient being evaluated is obtained from the spectrum and is proportional to the square root of a sealed spectral area, the power spectra area being proportional to the square of the signal voltage.

In various embodiments, the one or more normalization ranges can be predefined ranges, sack as, merely by way of example, 30 to 40 cycles/minute.

In various embodiments of the method, artifacts and aberrant data patterns may include any one or more of peaks, peak edges, or excessive slopes that are aberrant in comparison with previously acquired data sets. By way of examples, artifacts and aberrant data patterns may be identifiable as originating from any one or mote of stomach, small intestine or colonic activity, respiratory activity, heartbeats, and/or frequency harmonics of same. Artifacts and aberrant data patterns may be identified by (a) calculating a spectrum and (b) determining whether there are any regions with slope greater than a limiting value, wherein the slope determination comprises sufficient data points to effectively average out high frequency components. In another example, artifacts and aberrant data patterns may be identified by (a) calculating a spectrum, (b) smoothing the spectral data to remove high frequency noise to reveal an overall, shape, and (c) determining whether there are any regions with slope greater than a limiting value.

In some embodiments of the method, identifying the quiet section includes examining the range of the first derivative of a smoothed power spectrum. In particular embodiments, identifying the quiet section further includes examining the range of the second derivative of a smoothed power spectrum.

In some embodiments of the method, the normalization value is determined by a ratio of (1) the integral of she spectrum of the acquired gastrointestinal data set from the patient being evaluated over (2) the integral of the normalization reference data spectrum determined to be quiet, said normalization spectrum modeled by a table of values or by a mathematical function fitted to the data.

In some embodiments of the method, the electrode patch has multiple electrodes, the method comprising normalizing the amplitude of gastrointestinal data acquired from each of the multiple electrodes independently. In other embodiments, the electrode patch has multiple electrodes, the method comprising grouping the acquired gastrointestinal data from the multiple electrodes into a single grouped data set, the method comprising normalizing the single grouped data set.

Embodiments of the method make use of the full data set, coming from multiple patches, in different ways. By way of example, with three patches, normalization can occur patch-by-patch, using reference sets that are associated with a patch-specific identifier such as the location on the abdomen. Alternatively, all patches can be normalized separately but in reference to the standard data set, or group all the patches together into one set to determine a single normalization value. Accordingly, in alternative embodiments, normalization could make use of a single, consolidated reference, or normalization could be individual patch-specific.

Embodiments of the disclosure are directed to a method of characterizing parameters of peaks in the frequency spectrum of a gastrointestinal EMG data set acquired from an electrode patch mounted on a skin surface of a patient. Method steps include calculating a series of frequency spectra within the EMG data set using sequential time series segment subsets, and setting first and second thresholds based on a calculated spectrum within the acquired data.

A first threshold is applicable to identifying a background or baseline amplitude; a second threshold is higher than the first threshold, and is applicable for identifying peaks in the data set, wherein both first and second thresholds are determined based on values in the calculated spectrum within the data set. Method steps further include locating points within the data set that are above the amplitude of the second threshold by way of a known peak detection algorithm to yield one or more identified peaks; applying a set of "cuts" to the one or more identified peaks, and calculating the volume above the baseline amplitude of each identified peak in each sequential time segment. Method steps further include segregating the identified peaks into subsets based on any one or more of (1) predetermined frequency ranges associated with motor activity of specific gastrointestinal organs or (2) time periods as identified by patient activity; and summing the volumes of all peaks within the data subsets. The time periods referred to may include any diurnal aspect of the time during which data are acquired or any gastrointestinal event, such as eating a meal.

In some embodiments of the method, the first threshold is determined in terms of percentile rank of all the spectral data set points, and the peak threshold is based on a second, higher percentile rank. Further, in some embodiments, the background value and peak threshold are based on predetermined fixed percentages of the highest and lowest values.

In some embodiments of the method, the one or more known peak detection algorithms is any one or more of a simple threshold peak detector, a piecewise threshold peak detector, a peak detector that employs quadratic fits, a peak detector that imposes simple constraints such as requiring consecutive values above threshold, a peak detector that provides smoothing prior to peak detection, or any other suitable approach.

In some embodiments of the method, the cuts are based on any one or more of absolute spectral amplitude values, on net amplitude values with background subtracted, on net amplitude values scaled in terms of the background value, on having a minimum distance in frequency units from an adjacent peak, on having a minimum distance from a boundary of the spectral region, on having a structural shape such that the sides of the peak as they drop below the peak threshold continue to decrease to less than some specified fraction of the maximum value before again crossing the peak threshold, thereby establishing that the peaks are indeed separate.

In some embodiments of the method, the spectrum amplitudes are scaled by the frequency to improve the detection of higher frequency peaks that often have lower amplitude in a sub-range that may have more than one peak.

In some embodiments of the method, the spectral range is broken into several meaningful sub-ranges, with different sets of threshold, peak detection, and cut criteria control values in each, such sub-ranges representative of known physiologic activity, for example of activity from the stomach, small intestine, and the colon, where the summing or combining of peaks and their parameters is based on which sub-range the peaks are in. In particular examples of these embodiments, the sub-ranges are defined based on knowledge of the typical location of spectral peaks, each sub-range encompassing one peak. In other examples, the subranges overlap one another to avoid discrimination against peaks that are near the boundary due to requirements of the peak selection cuts.

In some embodiments of the method, the time segment length is a predetermined number of minutes chosen to optimize over the competing needs of the overall s/n, peak resolution, and ability to capture brief events. In other embodiments, the time segment length is a fixed value, but the start times are staggered by an offset in successive analysis runs to improve the detection of shorter peaks by better synchronization of the time segment with their duration in at least one of the runs. For example using a segment n minutes long, the analysis would be run n times, starting at t=0 min, t=1 min, t=2 min, etc.

Further in regard to time segment lengths, in some embodiments the multiple analysis runs are performed first with one segment length and with sequential offset values, then the same sequence is repeated with the next segment length in a series such as 1, 2, 4, 8 . . . minutes, in order to optimally detect all existing peaks and their start and end times. And in some embodiments, the time segments used for analysts are not fixed but are rather selected to fit the start and end time of peaks based on pre-analysis peak detection using several different fixed time segment lengths, or a sliding fixed length, or one of the other techniques described herein.

With regard to multi-channel data, in some embodiments of the method, the data set includes multiple channels, and the frequencies observed in different channels are grouped into sets defining a frequency group based on their proximity to one another, and the summing of peak volumes is based on the frequency group. In some embodiments, the grouping can be accomplished by creating a histogram of the peak frequencies and performing a peak detection analysis on the histogram, thereby identifying separate groupings of peak frequencies that can be treated as related to one another within each grouping.

Further, in some embodiments wherein the data set includes multiple channels, and wherein the peak frequency grouping includes a selection of one or more of such multiple channels, the peak volumes are summed over all selected channels.

DETAILED INSCRIPTION

The following description of the preferred embodiments is not intended to limit the invention to these preferred embodiments, but rather to enable any person skilled in the art to make and use this invention. Disclosed hereto are systems and methods for processing electromyography signals of the gastrointestinal tract.

System

Figure 1:
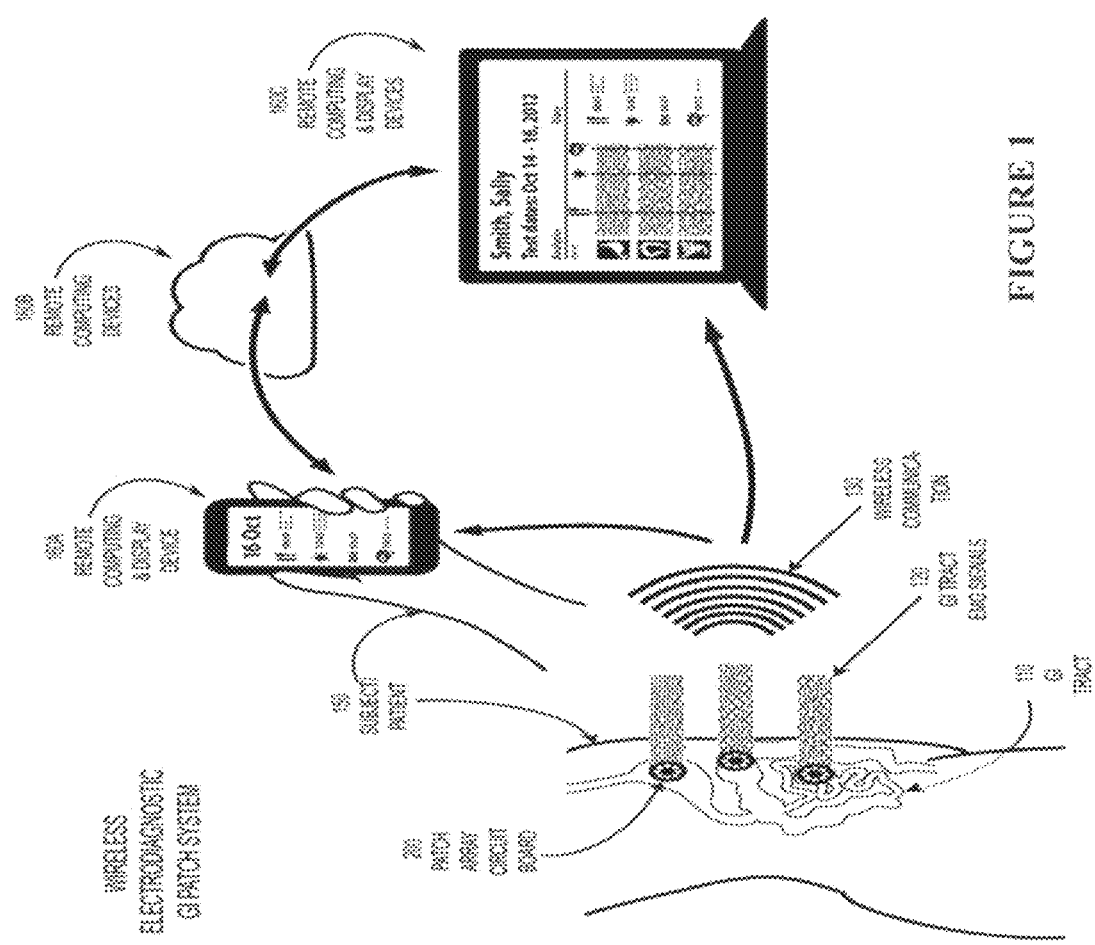
FIG. 1 illustrates a schematic diagram of one embodiment of a wearable, wireless, GI electrodiagnostic data aggregating and diagnostic system.

FIG. 1 schematically illustrates one embodiment of a wearable, wireless, GI electrodiagnostic data aggregating and diagnostic system. In some embodiments, the system includes: a patch 200 for acquiring signals from the GI tract 110 of a pattern 150, a handheld computing device 160*a* (e.g., mobile phone, tablet, etc.) for supplemental data entry by a patient or other user, one or more remote computer servers 160*b*, and one or more remote computer/display devices 160*c*. In various embodiments, electrical signals 120 of the body are acquired by the patch 200, patient symptoms and activity are entered by a user of the handheld computing device 160*a*, and data indicative of the electrical signals and user-entered information are wirelessly transmitted 130 to the remote computer servers 160*b* for data storage and optional processing. The data is further accessed by, and optionally transmitted to, the remote computer/display device 160*c* for further processing and/or display. In some embodiments, the processed data is displayed as a table or plot of EMG activity and for doctor diagnostic assistance. In some embodiments, the system includes one or more features of the systems described in U.S. application Ser. No. 14/051,440, titled "Wearable wireless patches containing electrode pair arrays for gastrointestinal electrodiagnostics," filed Oct. 10, 2013, which is herein incorporated by reference in its entirety.

Figure 2:
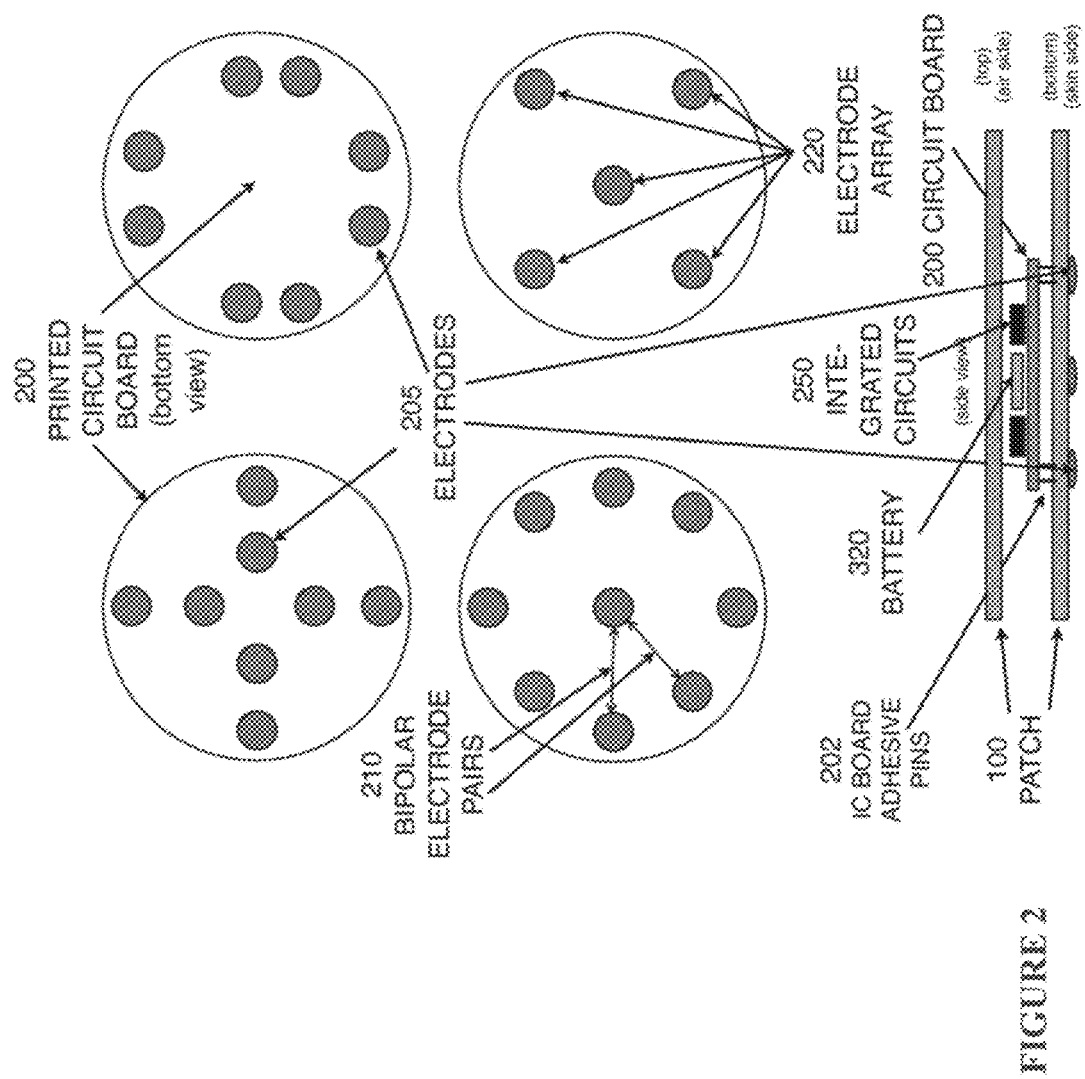
FIG. 2 illustrates a schematic diagram of one embodiment of a multi-electrode configuration of a wearable, wireless, GI electrodiagnostic data aggregating and diagnostic system.
Figure 3:
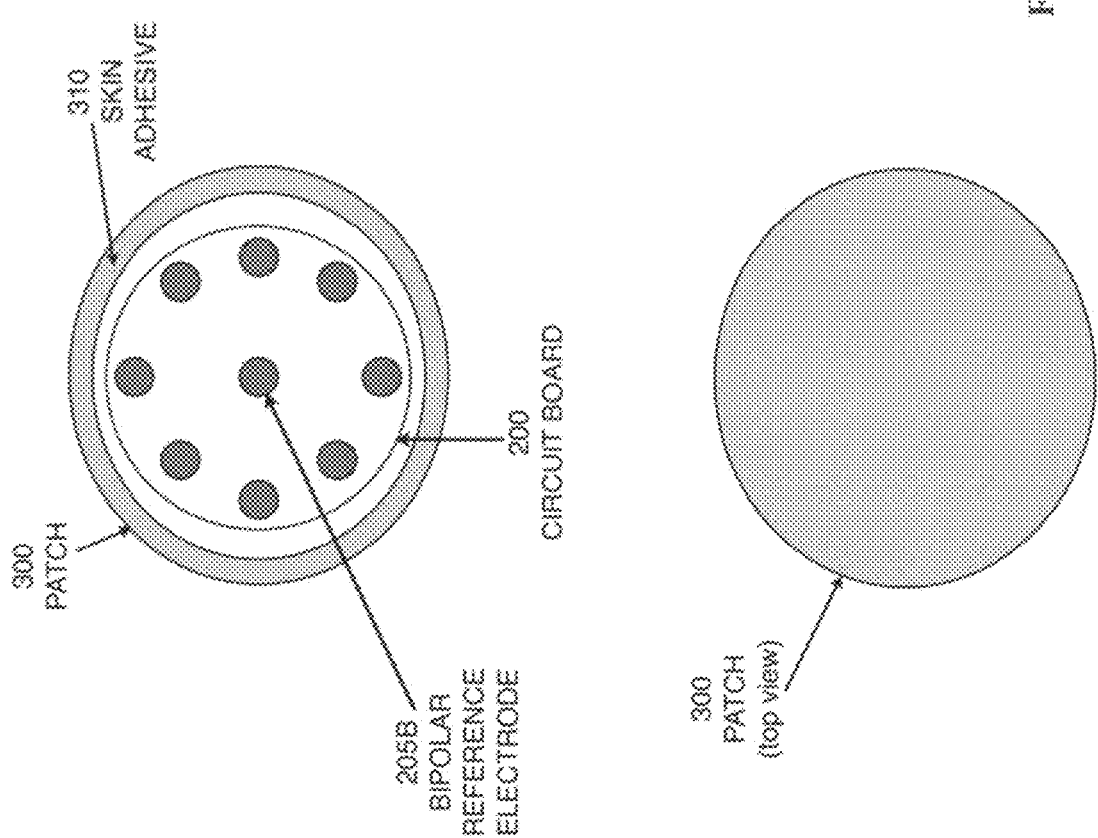
FIG. 3 illustrates a schematic diagram of a simplified bottom view of one embodiment of a patch of a wearable, wireless, GI electrodiagnostic data aggregating and diagnostic system.

FIGS. 1-3 each presents a system wide view, with a set of multi-day-wearable patches 300/200/100 that sense and digitize myoelectric data 120 at the skin surface 150 originating in the smooth muscles of the stomach, small intestine, and colon, 110 and transfer the data wirelessly 130 to a handheld computing device 160*a*. The patches include two or more bipolar pairs of electrodes 205 arranged substantially orthogonally. The bipolar pairs of electrodes are configured to sense and acquire EMG voltage signals. Further, the patches include onboard sensors that are capable of measuring acceleration, velocity, and/or position 402. The sensors of some embodiments include one or more of accelerometers, GPS sensors, and gyroscopes. Also, as shown, the patches of various embodiments include a circuit hoard 200, which includes integrated circuit components 250 and a battery 320 to supply power to the patch. The integrated circuit components 250 of various embodiments include a microprocessor and one or more signal processing components such as an operational amplifier and AC-DC converter, which function together to digitize, amplify, and optionally, filter or otherwise process the acquired voltage signals. The integrated circuit components 250 further include a wireless antenna for modulating and demodulating digitized data for wireless signal transmission. In various embodiments, the wireless antenna is a radiofrequency (RF) antenna configured to wirelessly receive and transmit digital signals to the handheld computing device 160*a*. In some embodiments, the RF antenna is a Bluetooth®, low energy Bluetooth® antenna iBeacon, nearfield communication antenna, or any other suitable RF antenna configured to transmission of signals from the patch to the handheld computing device 160*a*.

The computing device 160*a* is capable of allowing the patient to enter activity and symptom information relevant to their gastrointestinal (GI) tract such as meal contents, bowel movements, and/or abdominal pain, synchronizing and combining this information with the time-stamped raw data 120 and uploading both to a cloud server 160*b* or other wireless host. The host serves as a repository of data. The host 160*b* may also serve as a processing device for further processing; in such embodiments, the host 160*b* may perform various methods described herein, and highly processed data is available for download for viewing or further manipulation on one or mare remote confuting and display devices 160*c*. Alternatively, relatively unprocessed data may be downloaded to a remote computing and display device 160*c* for further processing. In such embodiments, the remote computing and display device 160*c* serves as the processing device configured to perform various processing methods described herein.

The processing device of various embodiments is a laptop, tablet, desktop computer, server machine, or other computing device. The processing device uses time and frequency based algorithms to extract events and patterns of events that relate to the activity of the aforementioned GI organs 120, specifically slow waves that are associated with mixing and propulsion of then contents as part of digestion and elimination, with the purpose of providing diagnostic information on the activity of the organs as they relate to functional GI disorders (FGIDs) such as irritable bowel disorder (IBS). In some embodiments, the processing device performs artifact removal, normalization, and characterization of the extracted events and patterns that relate to the activity of the GI organs, as will be described in greater detail below. The computing device further includes the ability to coordinate data transfer schedules with the patches to accommodate either regularly scheduled transfers 404 or reconnecting when temporarily out of range, and the further ability to identify patches individually.

The processing device of various embodiments includes a processor, which may be a general purpose microprocessor, a digital signal processor (DSP), a field programmable gate array (FPGA), an application specific integrated circuit (ASIC), or other programmable logic device, or other discrete computer-executable components designed to perform the functions described here. The processor may also be formed of a combination of computing devices, for example, a DSP and a microprocessor, a plurality of microprocessors, one or more microprocessors in conjunction with a DSP core, or any other suitable configuration.

In various embodiments, the processor is coupled, via one or more buses, to memory in order to read information from and write information to the memory. The processor may additionally or alternatively contain memory. The memory can include, for example, processor cache. The memory may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include software stored in a non-transitory format. The software, when executed by the processor, causes the processor to perform one or more operations described elsewhere herein.

In various embodiments, the remote computing and display device 160*c* includes: a wireless communication connection to access data from the remote server 160*b*; and a touchscreen, monitor, LCD screen, or other monitor configured to graphically display the processed data to a physician or other healthcare professional. The processed data of some embodiments is displayed on the remote computing and display device 160*c* in a line graph, table, or other output format that can be quickly and easily interpreted and understood by a healthcare professional. In some embodiments, the displayed data is used to facilitate diagnosis or monitoring of one or more gastrointestinal disorders.

FIG. 2 schematically illustrates the electrode array circuit board 200. In some embodiments, the disposable unit 200 includes two to ten embedded bipolar pair electrodes 205. In one embodiment, the disposable unit 200 has at least two embedded bipolar pair electrodes 205. In one embodiment, the disposable unit 200 has eight embedded bipolar pair electrodes 205 arranged in an array 220. In some embodiments, the inter-electrode distance is between 1 and 2 inches. The electrodes 205 are embedded inside the printed circuit board patch unit 200, with an ideally slight extension for greater skin contact. In some embodiments, the circuit board 200 is entombed in waterproof resin for greater water resistance. Further, in some embodiments, the patch housing itself 300 includes water resistant properties.

FIG. 3 shows a bottom and top view of an exemplary patch 300 and electrode array circuit board 200. Long-term non-invasive GI tract monitoring, an inexpensive, light, water-resistant, and disposable skin-adhesive unit 100 is provided. Because the unit is disposable, it can be easily replaced with another disposable unit after its usage for a period of time (e.g., hours, days, weeks). In some embodiments, the bottom of the disposable unit 100 has an adhesive surface 110 that can be affixed to the patient's skin for 7-14 days. In one embodiment, the bottom of the disposable unit ion can be affixed to the parent's skin for at least 7 days. In some embodiments, the adhesive includes a drying adhesive (e.g., white glue, rubber cement, contact adhesives), pressure-sensitive adhesive, contact adhesive (e.g., natural rubber, neoprene), hot adhesive (e.g., hot glue), or multi-part adhesive (e.g., Polyester resin and polyurethane resin, polyols and polyurethane resin, acrylic polymers and polyurethane resins). In one embodiment, the adhesive is a pressure-sensitive adhesive, which forms a bond when pressure is applied to stick the adhesive to the adherent (e.g., the patient's skin).

The patches, as shown in FIGS. 1-3, acquire myoelectrical data in the form of voltage readings that represent electrical activity of the digestive organs. Inevitably, the electrode patches also sense and record electrical activity from other biological sources, such as the heart and skeletal muscles. Due to the sensitivity required to measure the microvolt level signals from the digestive organs, artifacts can be induced by interactions between electrodes and skin surface, for example by way of transverse slippage or partial separation. At least some of these artifacts can be much larger in amplitude than the signals of interest. Further, these recordings, taken over a period of many hours or even days at frequencies of several Hz or more, and on multiple channels, result in very large data sets, with tens to hundreds of millions of individual readings. Interpreting these data and providing a clinically valuable summary is a significant challenge, which is addressed by the presently disclosed systems using one or more of the methods described herein.

Artifact Removal

The presence of such artifacts, particularly ones with high amplitude, negatively affects subsequent processing intended to reveal valid physiological data. For example, even a small number of large artifacts can have a profound affect on a frequency spectrum of the data, and make it difficult to identify rhythmic peaks that relate to the gastrointestinal motor activity of primary interest. Accordingly, a method for identifying and eliminating such artifacts with minimal disturbance of underlying valid gastrointestinal signals in data sets acquired from electrode patches is now provided.

Figure 4:
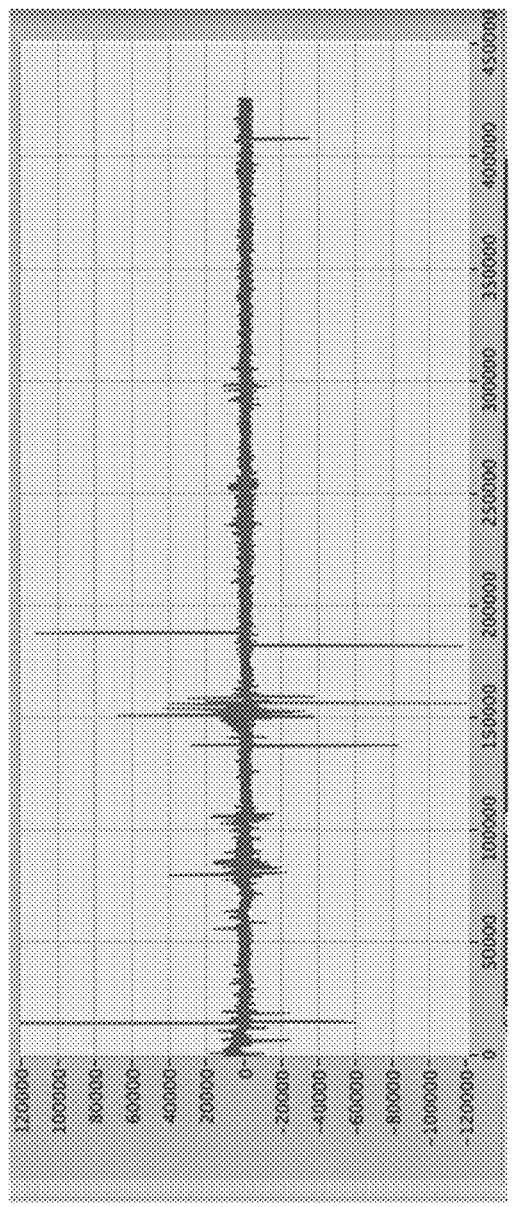
FIG. 4 shows a raw, un-cleaned electrode data set, showing both artifacts and periods of clean data.
Figure 5:
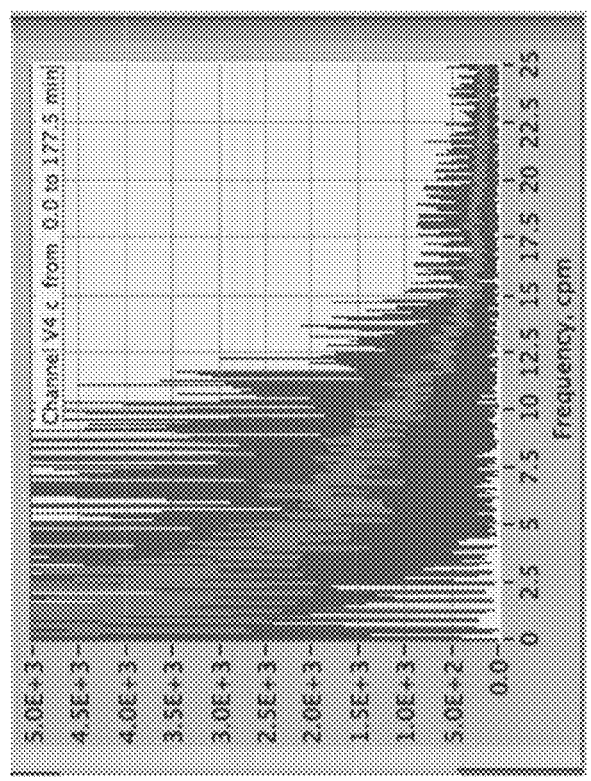
FIG. 5 shows power spectrum of the data set in FIG. 4; the red trace represents a moving average of the blue data series.
Figure 6:
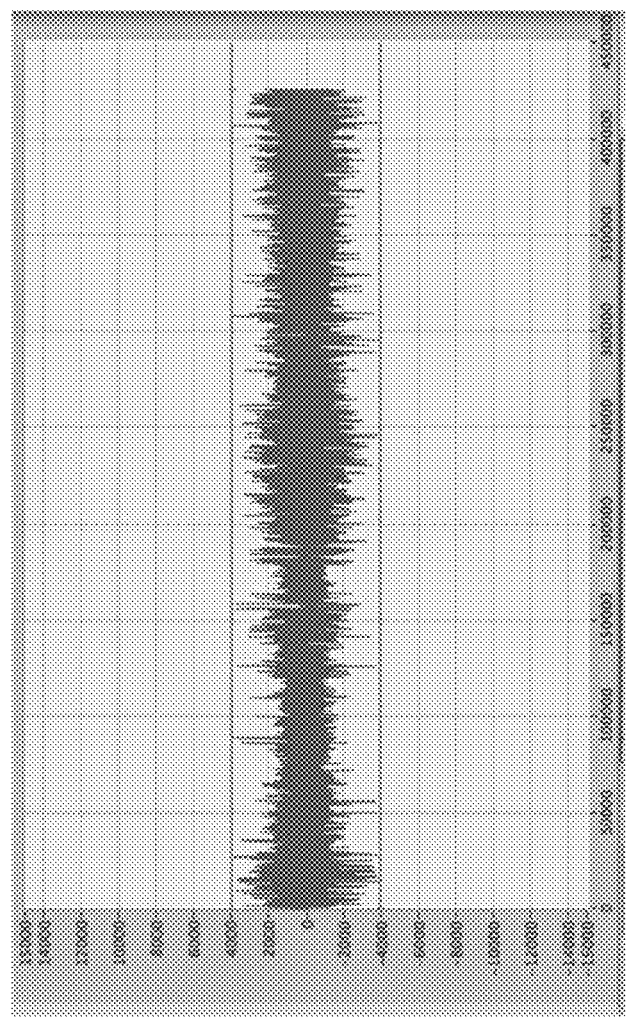
FIG. 6 shows data of FIG. 4 after artifacts have been removed using the methods described herein. Note scale change from FIG. 4.
Figure 7:
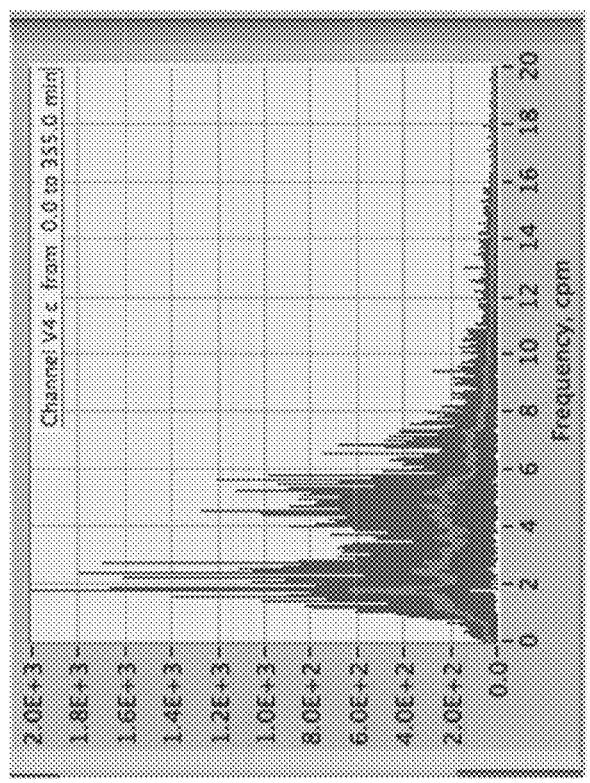
FIG. 7 shows spectrum of cleaned data in FIG. 6. Structures are now evident. Red trace represents a moving average of the raw spectrum shown by the blue data series.

A representative sample data set is shown in FIG. 4, representing 3 hours acquired at 40 Hz. The vertical axis is amplitude in ADC counts while the horizontal axis is point number representing time. The large amplitude spikes or peaks are artifacts. The data of interest are all contained in the much lower amplitude areas. Note that the number of data points over 400,000 are far more than can be individually discerned due to print or screen resolution; this tends to visually exaggerate the time extent of the artifacts. Nevertheless the effect of artifacts on the analysis is profound. One of the most useful approaches to interpreting the data is to create a power spectrum by last Fourier transform (FFT). FIG. 5 shows the power spectrum of the data in FIG. 4. It is lacking in useful information due to the artifacts. By contrast FIG. 6 shows the data set from FIG. 4 after artifact cleanup (note scale change) and FIG. 7 the spectrum. The cleaned spectrum is substantially different and it is possible to see structures that are ultimately useful for the purposes of the measurement, for example understanding the motor activity of the gastrointestinal (GI) tract.

Figure 8:
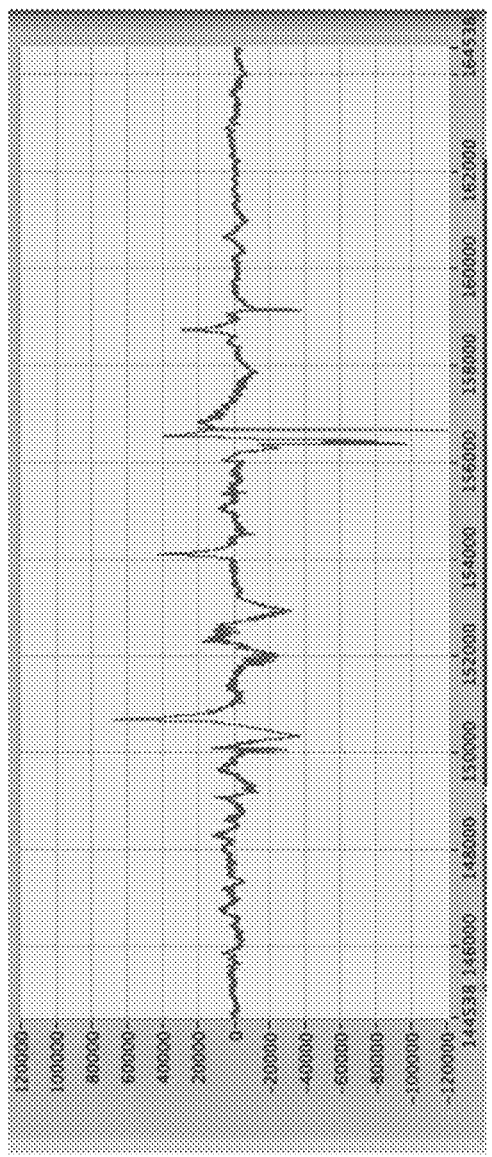
FIG. 8 shows 50 seconds of data showing structure of the artifacts.

By displaying a shorter section of the data one can better see the structure of artifacts and the fact that they come in several different flavors or patterns. FIG. 8 is an example of 50 seconds of dam from the same data set. There are approximately five artifacts shown, depending on how the artifact and its extent in time are defined. While some of the large amplitude peaks are easy to identify as artificial others are less clearly so. The field of gastrointestinal tract diagnosis from surface electrical measurements, in particular, is so new that there is still no clear definition of what is an artifact and what may be an interesting signal. This underscores the importance of maintaining a flexible system far artifact removal.

Figure 9:
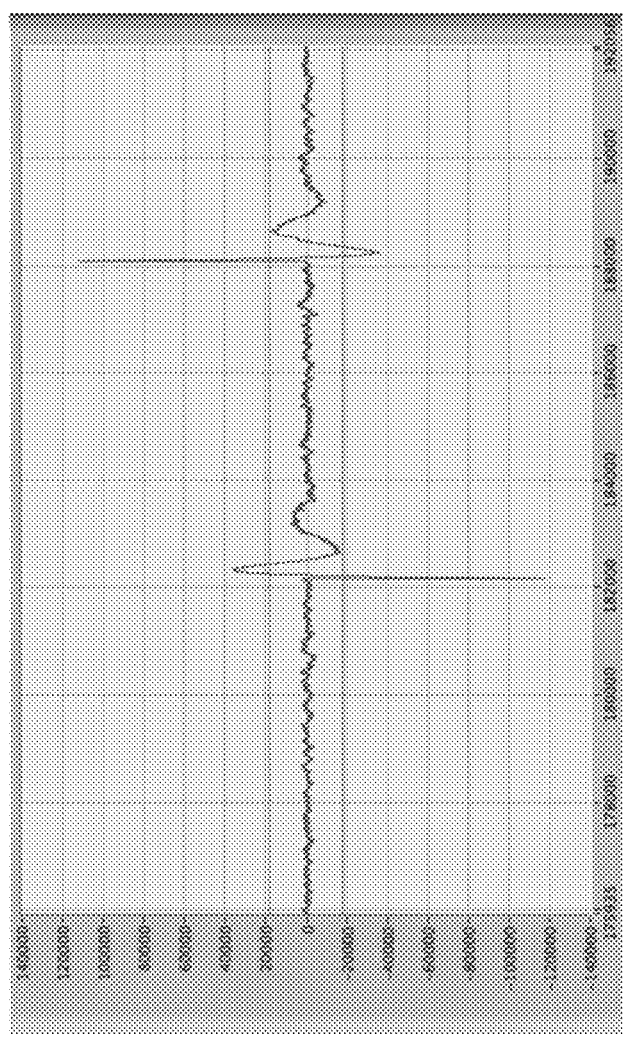
FIG. 9 shows artifacts with a particular shape.
Figure 10:
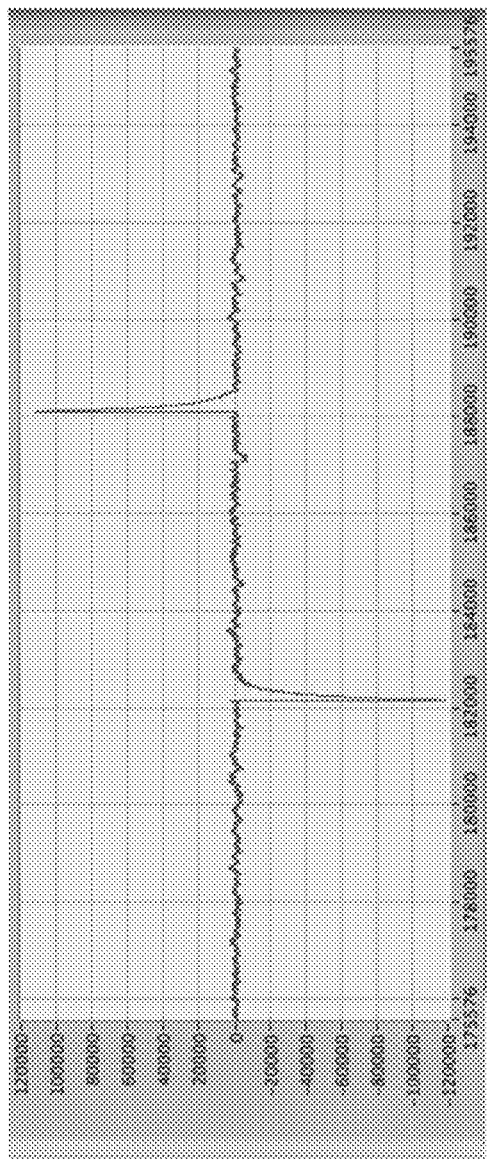
FIG. 10 shows artifacts with another particular shape.

However, while there are many sources and resulting forms of artifacts, there are also some shapes that repeat. FIGS. 9 and 10 show examples of shapes that are often seen, in both cases with inversion of the second relative to the first. Thus while identification of artifacts is ultimately based largely on amplitude as the primary characteristic, it can also involve shapes of patterns of the event. Not shown in the figures, but occurring occasionally, is a type of simple artifact such as those known to arise from errors in the digitization circuitry of the analog-to-digital (ADC) conversion, which involves a single point of very large positive or negative amplitudes. These artifacts are easy to identify by their amplitude and narrowness, and can be eliminated by setting the value to the average of the points on either side. In the case of two or more consecutive points that meet the description, the same identification and resolution may follow.

Measurements of electrical signals from human subjects and other mammals are dependent on many factors, including the quality of the skin, skin preparation, amount of adipose tissue, distance from the source to the measurement point, and so forth. These dependencies lead to significant differences in the amplitude of the signals of interest. Thus it is impossible to select a single absolute value as threshold for identifying an artifact. Rather one must use the data itself as a means of determining the threshold. The well practiced human eye-mind system is quite good at this; one can look at the clean sections of the data and say here is where you should set the threshold, but an automated computer system needs an algorithm with some sophistication to deal with variation between subjects as well as variability during a single test, either between electrodes or as a function of time.

One approach is to use the standard deviation (sigma) of the data, for example setting a threshold such that anything beyond approximately 5-sigma indicates the presence of an artifact. Note that the full extent of the artifact, is not specified at the point in the process; depending on one's definition and interest in subsequent processing, only a portion of it may be above the threshold. For data sets with few artifacts the simple one-pass threshold based on a set sigma value is an effective approach. However for many data sets seen in practice, the sigma value is strongly influenced by the values carried by artifacts themselves, and the results one obtains after removal among multiple sets will be inconsistent depending upon the number and size of artifacts in each set. A solution to this issue is to remove the artifacts in a first pass, and then repeatedly apply the same criteria as defined in terms of the number of sigmas. As artifacts are removed in each pass, the calculated value of sigma is reduced, and the thresholds approach a value that would be obtained if there were no artifacts at all. For appropriate choice of number of sigma n (but not all), the process converges, that is, after some number of iterations of artifact removal and recalculation of sigma, no points lie outside the n sigma threshold.

That this situation should obtain with data sets of the type of consideration here can be understood by considering limiting cases. For n=2 for example, in a normal distribution 5% of all points will lie outside this threshold and as the largest values are removed the sigma calculate will continue to drop with the data values, until no points are left. On the other hand for an n such that only the very largest amplitude point is included, only a single iteration may be necessary. Thus one can understand that, in principle, there exists a range of n for which convergence will be achievable. This all depends on the data set having artifacts with much larger amplitude than the data of primary interest, and to some extent the value of n that is chose will depend on details of the data, including the number of points in the set.

Figure 11:
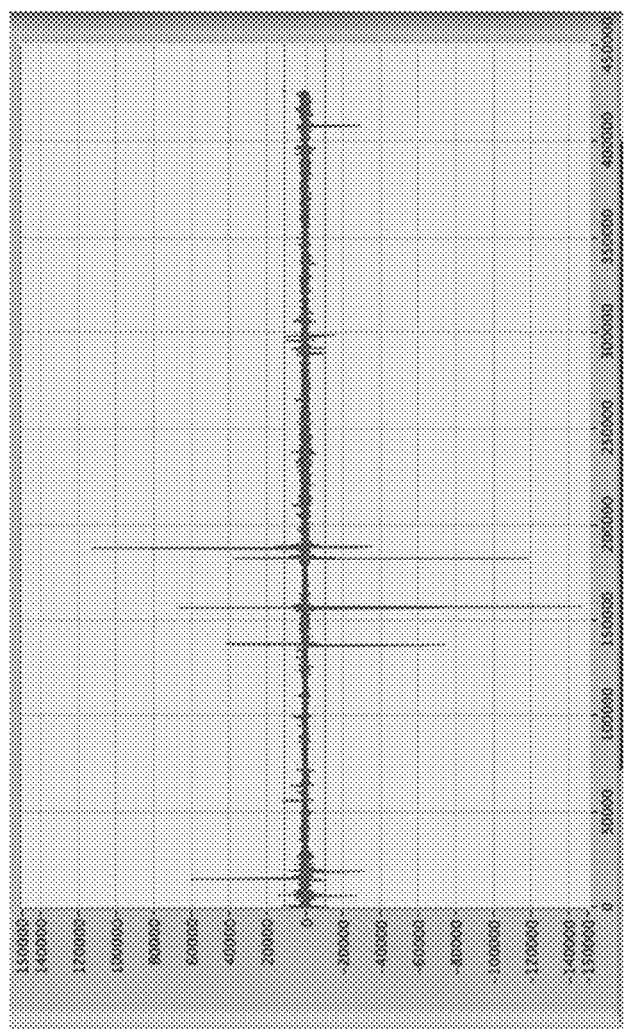
FIG. 11 shows a data set with, artifacts; the horizontal cursors indicate 5-sigma thresholds.
Figure 12:
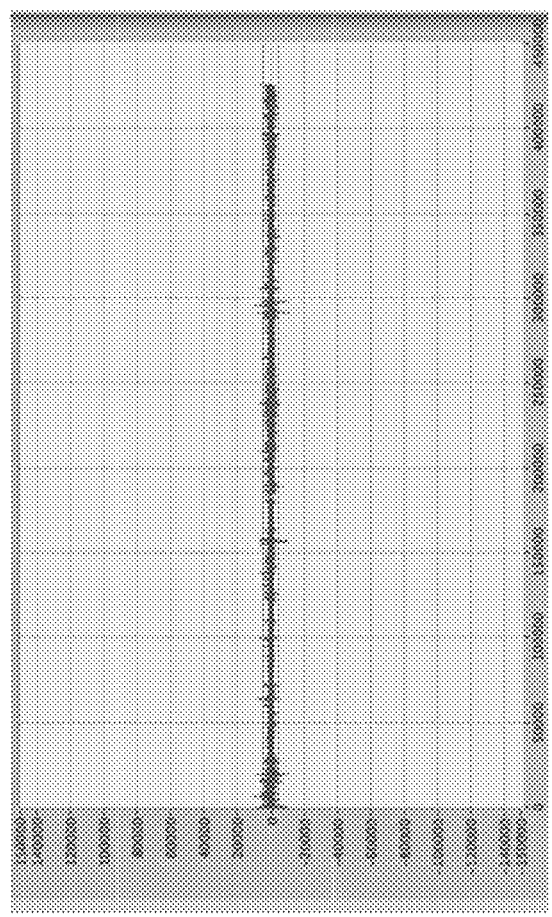
FIG. 12 shows the same data set as FIG. 11 after artifacts have been removed; cursors now show 5-sigma of the new data set.
Figure 13:
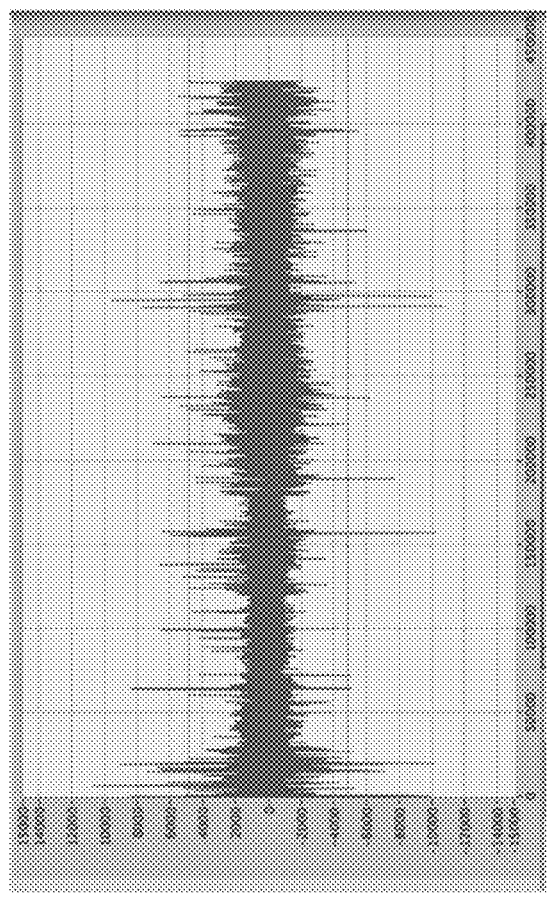
FIG. 13 shows the same data as in FIG. 12, zoomed in to show that artifacts remain, and how the 5-sigma threshold has shifted after first pass artifact removal.
Figure 14:
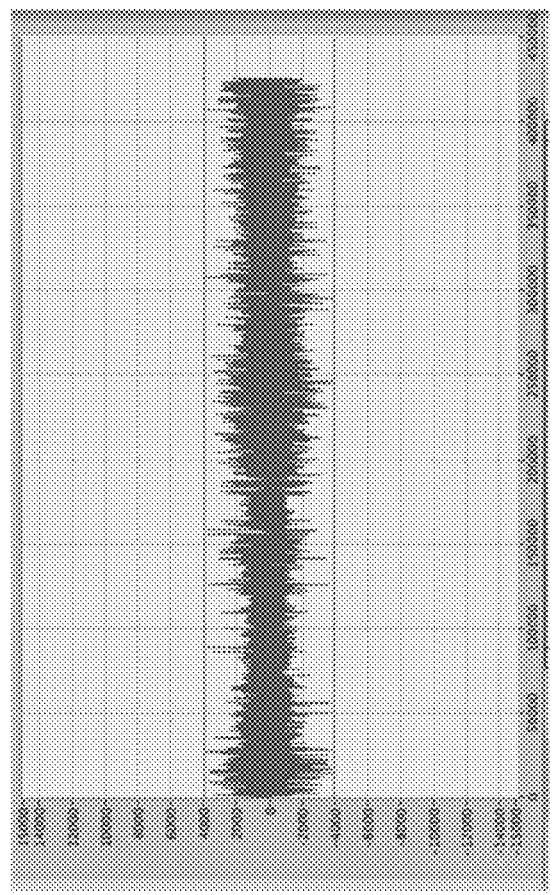
FIG. 14 shows the same original data set as in previous figures, after 6 iterations of artifact removal. Convergence has been achieved; there is no longer any point outside the 5-sigma threshold.

FIG. 11 shows an example of a time series data set where there are several very large amplitude events that are likely artifacts. The red horizontal cursors are set at the level of 5-sigma. The largest artifacts extend well outside the 5-sigma threshold. FIG. 12 shows the result after the artifacts identified by the 5-sigma threshold have been removed, with cursors set at the new 5-sigma level, which has been considerably reduced by the removal of the artifacts. FIG. 13 is the same as the previous FIG. 12, but the vertical scale zoomed in by a factor of 10-fold. Numerous points are now outside the new threshold. After these artifacts are removed, the results are shown in FIG. 14.

It is important to note that although the final threshold value can be arrived at without iteration, for example, by selecting an initial threshold n sigma less than 5, the exact value is not know able in advance. Each data set has its own characteristics, with the number, width and amplitude of artifacts, level of desirable signal, and so forth. The technique of iteratively removing artifacts using a fixed n allows the process to be used across a wide range of data sets yet lead to consistent results, as for instance measured by the ratio of largest to most probable absolute value.

An alternative approach to setting the threshold that similarly takes into account the values of the data is to use a percentile ranking, for example (negative-going) points that are below 2nd percentile and (positive-going) points above the 98th percentile. Other implementations of this approach include using the absolute value to make all values positive and then identifying artifacts by selecting those points above a given percentile.

Having identified the existence and location of a (potential) artifact by its amplitude relative to a threshold, it is possible to perform further analysis to shed further light on whether a time series event is indeed an artifact or is actually interesting physiologic data that one would preferably not remove. This is more likely with artifacts that are not much greater than the threshold than those that are, for instance, two or more times larger. One approach is to examine the pattern itself, comparing it to a known database of shapes of artifacts and real physiologic signals. FIG. 9 and FIG. 10 show examples of time series events that are known to be artifacts. It should be apparent that one can devise an algorithm that will establish the likelihood that a shape in question is from a set of artifacts or not, or from a set of known physiologic events or not, and make an automated judgment of whether to classify the event as an artifact or not. In case it is determined to most likely not be an artifact, one can have the algorithm not remove it even though part of it is larger than the amplitude threshold.

An additional source of information on whether a particular event is an artifact or interesting physiologic data is the distribution of its signal across multiple electrodes. Artifacts due to sudden motion, breathing, and skeletal muscle contractions can be distributed across multiple spatially separated electrodes in a recognizably different pattern from physiological signals. For example, if a signal has similar strength across well separated electrodes, it is less likely to be from a gastrointestinal organ than a surface muscle or from shifting of electrodes. Physiological signals typically have a peak channel where the strength is at maximum, and drop off in a gradual manner that has some dependence on the patient and some on the signal itself.

Figure 15:
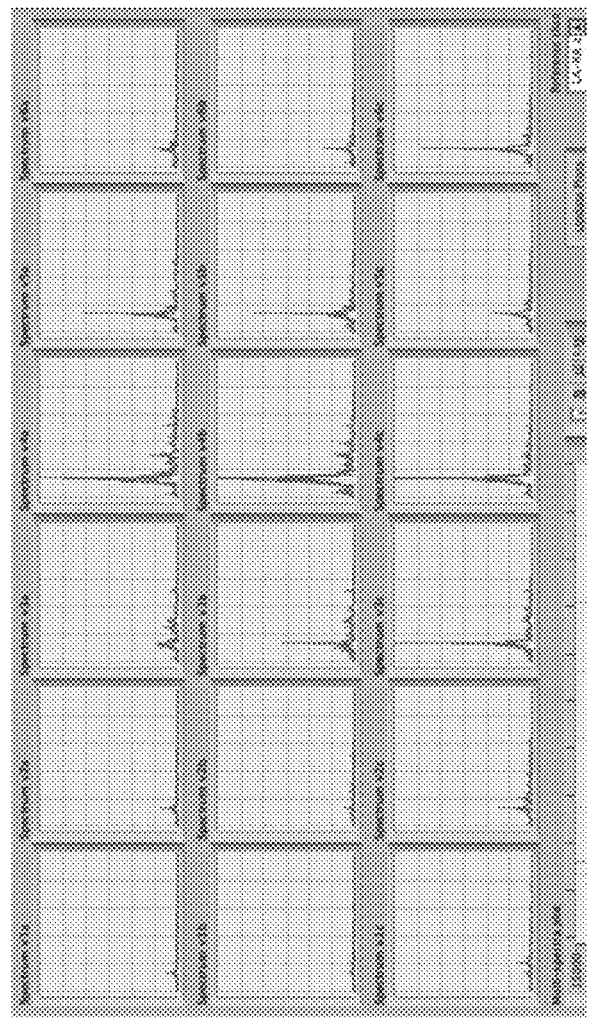
FIG. 15 shows individual Fourier power spectra from 18 electrodes spaced approximately 2 inches apart on subject's abdomen in three rows. The peak at 3 cycles per minute is from the subject's stomach, post meal.
Figure 16:
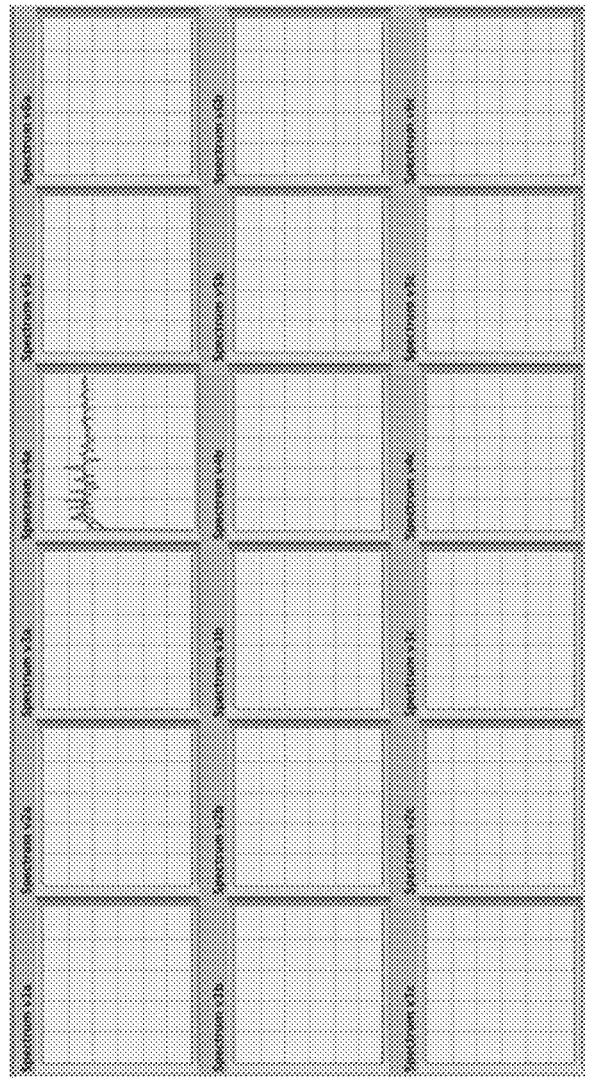
FIG. 16 shows individual Fourier power spectra from 18 electrodes spaced approximately 2 inches apart on subject's abdomen in three rows. Example of an artifact that shows up on only one channel.
Figure 17:
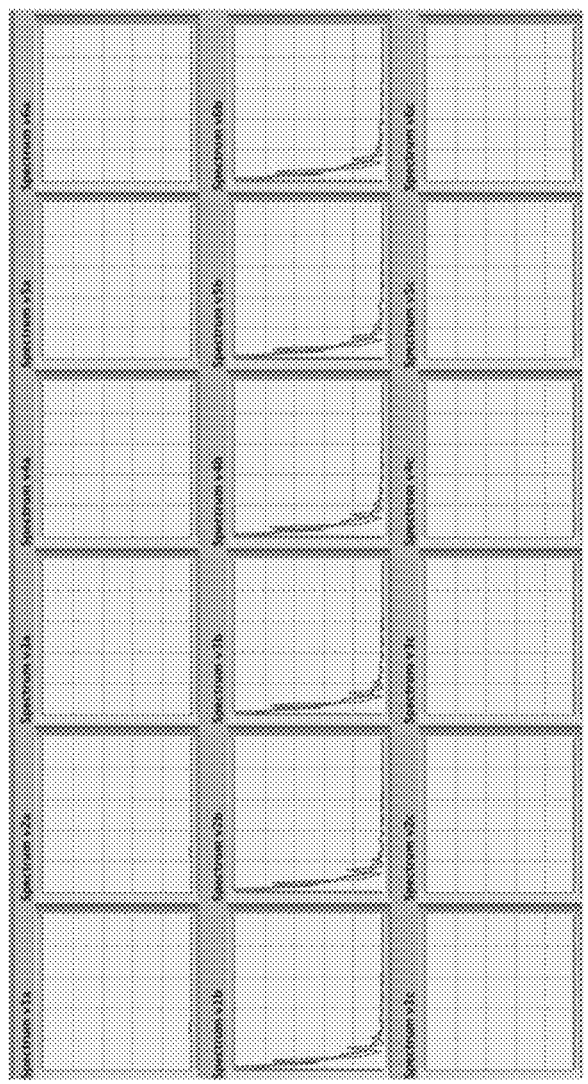
FIG. 17 shows individual Fourier power spectra from 18 electrodes spaced approximately 2 inches apart on subject's abdomen in three rows. Example of an artifact that shows up across a related group of channels.

FIG. 15 shows power spectra for 18 h electrodes placed on a subject's abdomen, in 3 rows of 6 electrodes, spaced approximately 2 inches apart. The peak that is visible at 3 cycles per minute is from the subject's stomach after a meal. While this is not a time series event, it is a real physiologic signal, and shows how such signals may be distributed spatially, with a maximum on one channel and gradually diminishing outwardly. An event that appears on only one channel, or on many channels with similar magnitude, is less likely to be of physiological origin. By contrast. FIGS. 16 and 17 show signals that are the result of artifacts, on only one channel, in FIG. 16, and on a group of related channels, in FIG. 17. It should be apparent from these examples that there are ways to examine and automatically process the distribution of data on multiple channels, whatever the physical arrangement of the channels, which provide independent information on the likelihood that an event is an artifact rather than interesting physiological data.

Once an artifact is identified by having one or more points beyond the chosen threshold, the task remains to remove it. To do so, the extent of its presence beyond the threshold must be determined. At its simplest, the signal can be "clipped", which replaces all the points above threshold by the threshold value. However this leads to a further set of problems in the spectrum, leaving sharp edges to create high frequency issues and a large low frequency component from the "flat top" clipped section. A somewhat better approach is to set all the values to zero, to avoid the lowest frequency component, but this worsens the edge issues, essentially taming them from sharp corners into knife edges and adding false energy into the high frequency spectrum. What is needed is a way to remove the artifact at its "roots" and replace is with values that are neutral or nearly so is the spectrum.

In this approach, the extent of the artifact is determined by tracking the points on both sides to their roots. For the sake of simplicity, we will assume a positive going artifact, with a data set midpoint of zero. It will be understood that the concept applies equally to negatively pointing artifacts and to data sets that have an average value with a non-zero offset. In this case the roots are at or near zero. Since the data are in discrete points, not a continuous function, it is highly unlikely that there will be a point with a value of exactly zero, but it will always be possible to find two points where a zero-crossing location can be interpolated between them. In this way, die extent of the artifact can be defined by the last (on the time axis) zero crossing before the artifact crosses threshold, and the first zero-crossing after it.

However, inasmuch as there is a great deal noise in some signals, the zero crossing as recorded may not be in the same location as in a noise free system, and this will give rise to inaccuracies in removing the artifact, either too little or too much being removed. To minimize the effect of noise, a filter can be applied to a copy of the data, for example a double sided moving average filter, or any other type of filter that removes high frequencies with little or no phase shift. This filtered copy is used to determine the location of the zero crossing, and the original data set is then processed using the location so determined. Typically one would use the point closest in time to the zero crossing location, but one could also intentionally introduce an offset in either direction to define either narrower or wider removal zones according to what one hopes to accomplish subsequently.

Once the extent of the artifact is determined, the next task is to replace it or simply remove it. Removal is inherently simple but introduces complexities in tracking the timing of later events, and if multiple channels of data are involved, either ruins the synchronization between them or forces the removal of all time periods that have an artifact on any channel, which may eliminate an unnecessary and excessive amount of data. It is desirable therefore to replace the artifact with values that have a neutral effect on the spectrum. In one approach all values are set to zero (or the mid-point if the average of the data set is non-zero) from the closest point to the zero-crossing on either side of the artifact. In another approach, the values in between the remaining edge points are linearly interpolated, leaving a slight slope. In a slightly more complex implementation, some number of points on either side of the artifact are smoothed and joined to the central section of all zeroes.

Figure 18:
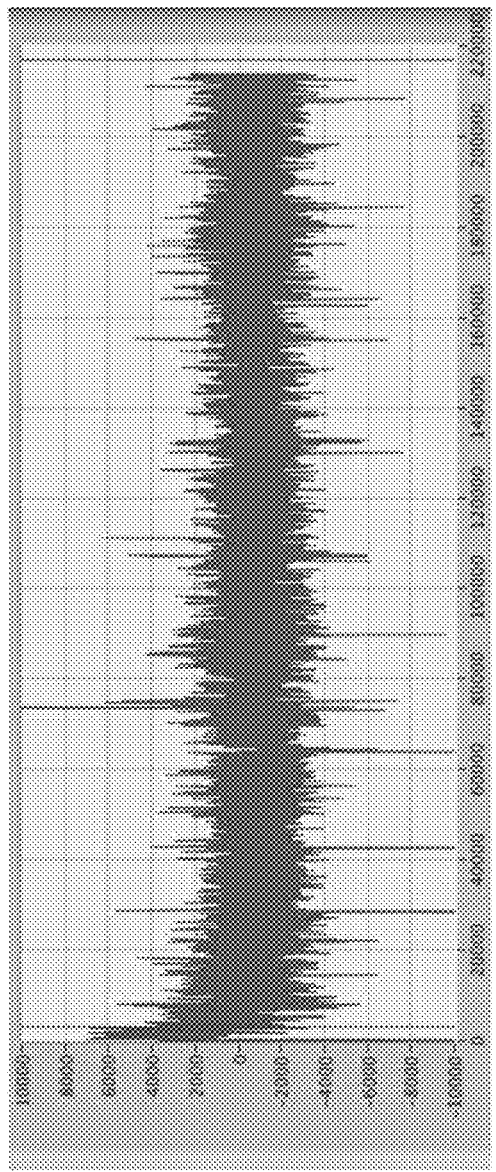
FIG. 18 shows a data set showing drift at the beginning of the test.
Figure 19:
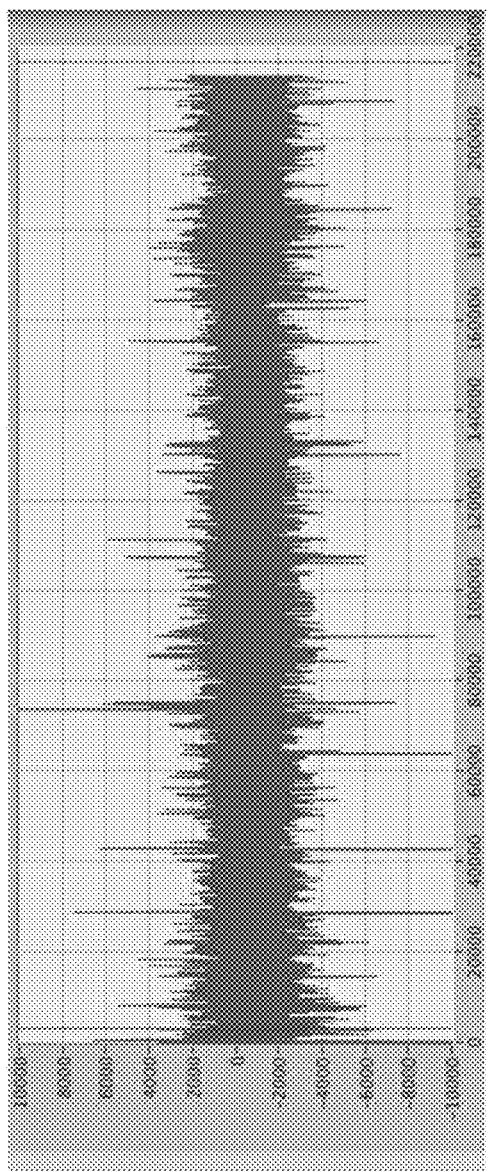
FIG. 19 shows the same data set as in FIG. 18 but with high-pass filter applied to remove the drift.
Figure 20:
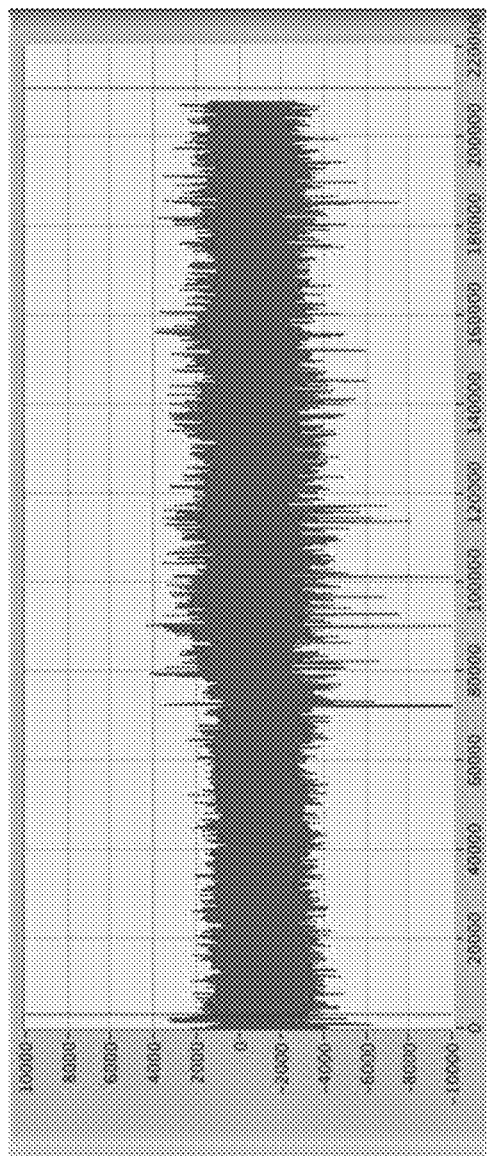
FIG. 20 shows a data set showing bias toward negative numbers due to high frequency repetitive signals.
Figure 21:
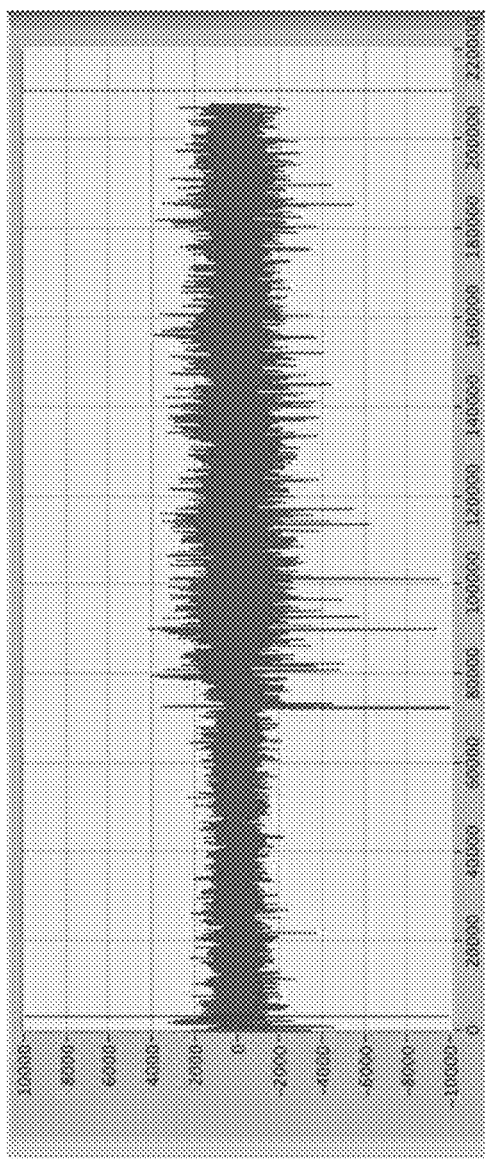
FIG. 21 shows the same data set as in FIG. 20 but with low-pass filter applied to remove negative bias.

Data sets that have very low frequency drift, whether only at the beginning or on a continuous basis, can present challenges to setting thresholds if the amplitude of the drill is not negligible compared to the amplitude of the signals of interest. In such cases, it is advantageous to apply a digital high pass filter at a very low frequency. Preferably, the filter cutoff frequency will be well below the frequencies of interest, for example at 0.5 cpm and with a low order (steepness) to minimize the inevitable phase shifts that are the result of filtering. Artifacts that are of the single data point, large amplitude type discussed earlier are best eliminated prior to such high-pass filtering as they will otherwise lead to a smearing of the artifact onto subsequent data points that are otherwise uncorrupted. Similarly, it can be advantageous to apply a digital low-pass filter to the data prior to the artifact removal step, to eliminate relatively high frequency signals such as those from heartbeats, which tend to bias the positive-negative symmetry and complicate the application of threshold determining schemes such as those based on a given number of standard deviations. FIGS. 18 and 19 show an unfiltered data set and the same set filtered with a high pass first order filter at 0.5 cpm. FIG. 20 shows a data set with bias toward negative values, in this ease front heartbeat signals, while in FIG. 21, a 4th order low-pass filter at 120 cpm has eliminated the bias. In both examples the unfiltered data set would compromise the effectiveness of the artifact threshold setting and ultimately set a lower limit on the amplitude of artifacts that could be eliminated.

Normalization

The overall strength of the signals obtained from the organs of the body through the layers of tissue and skin surface depends not only on the signal source itself, but also on details of the layers in between electrodes and source. The thickness and quality of tissue layers, the quality of skin and its preparation, and the coupling of the electrode to the skin all can have significant impact on the signal strength.

In order to make meaningful comparisons of signal obtained from a given subject against a standard or set of other subjects, it is necessary to take into account the individual sources of overall signal strength variability, and eliminate patient-to-patient variability as much as possible, and allow a clear comparison between any given patient and a well characterized normal population. Accordingly, a method for normalizing the recordings so that the effects of tissue layers and skin quality from patient-to-patient are mitigated is provided here.

Figure 22:
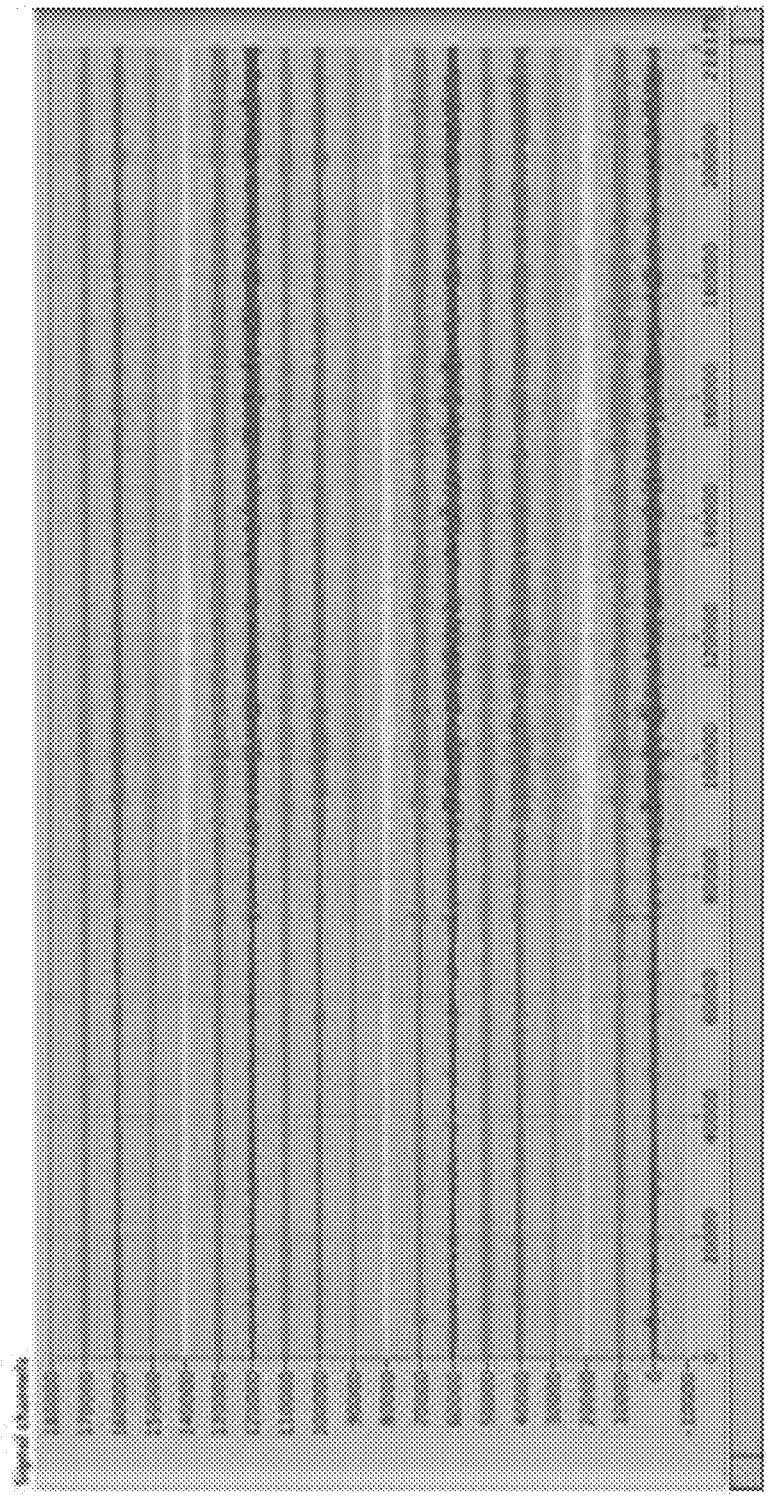
FIG. 22 shows a data set from Subject 027 before data normalization.
Figure 23:
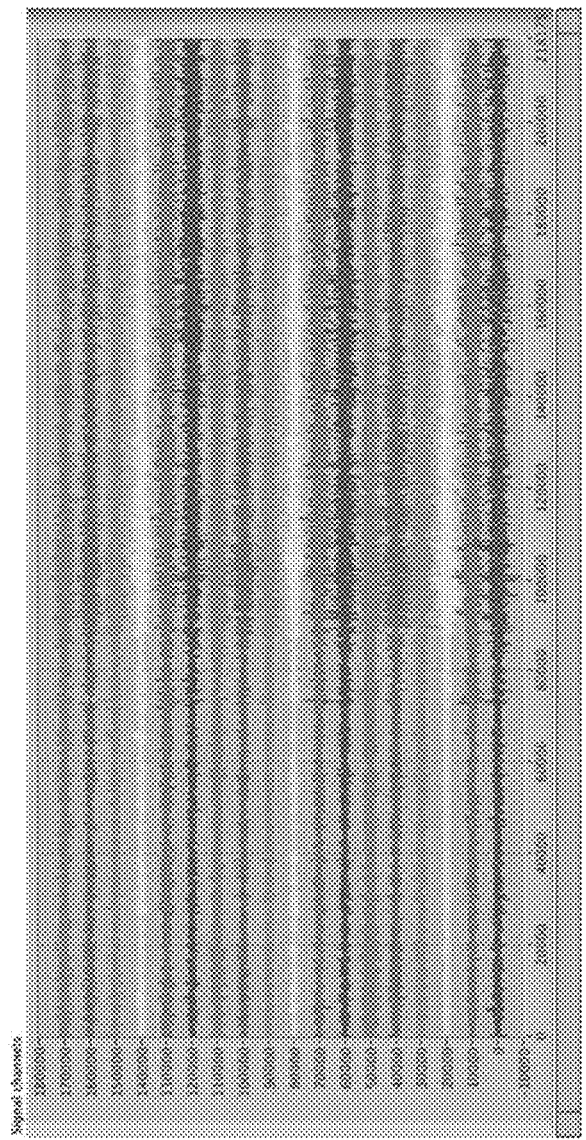
FIG. 23 shows a data set from Subject 027 after data normalization.
Figure 24:
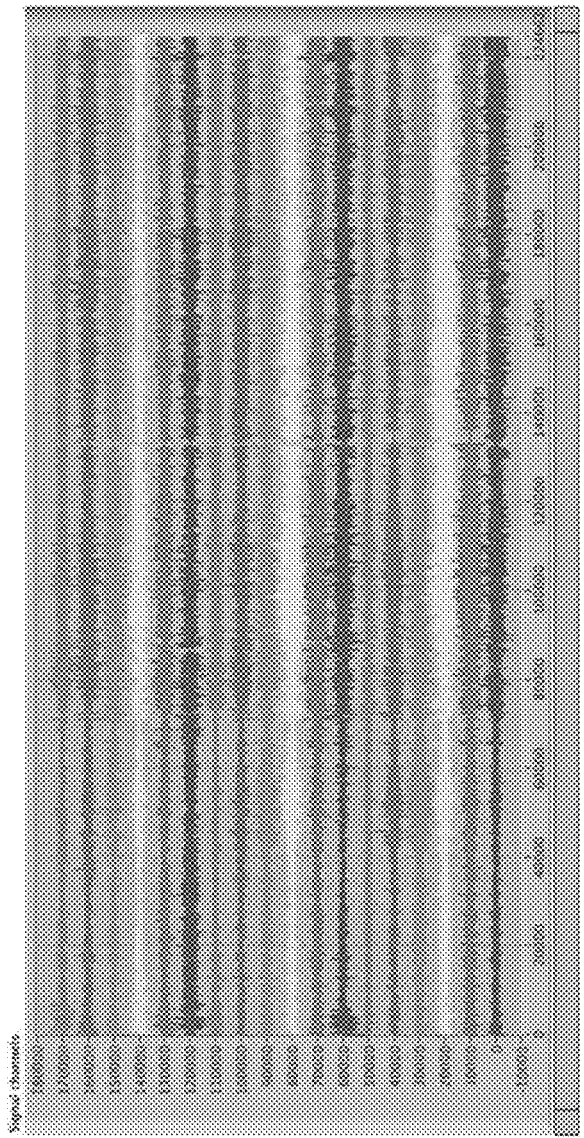
FIG. 24 shows a data set from Subject 013 before data normalization.
Figure 25:
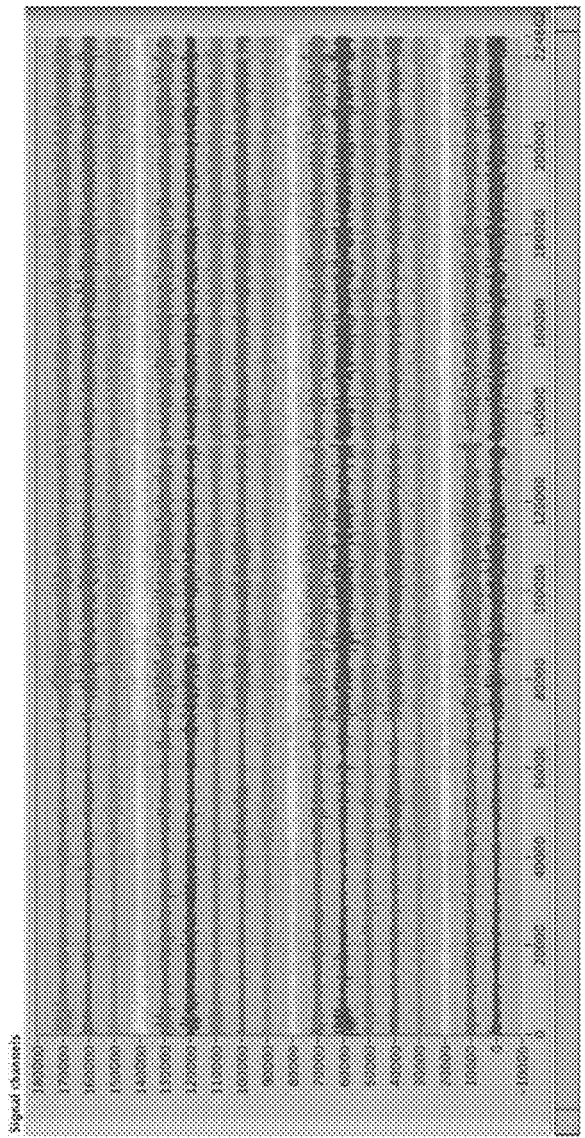
FIG. 25 shows a data set from Subject 013 after data normalization.
Figure 26:
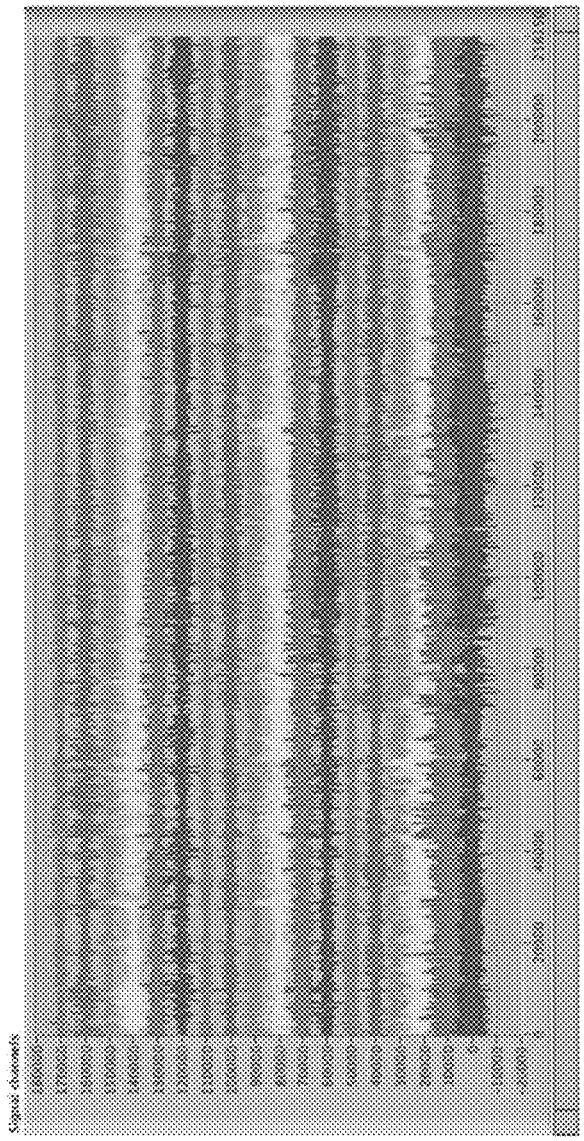
FIG. 26 shows a data set from Subject 012 before data normalization.
Figure 27:
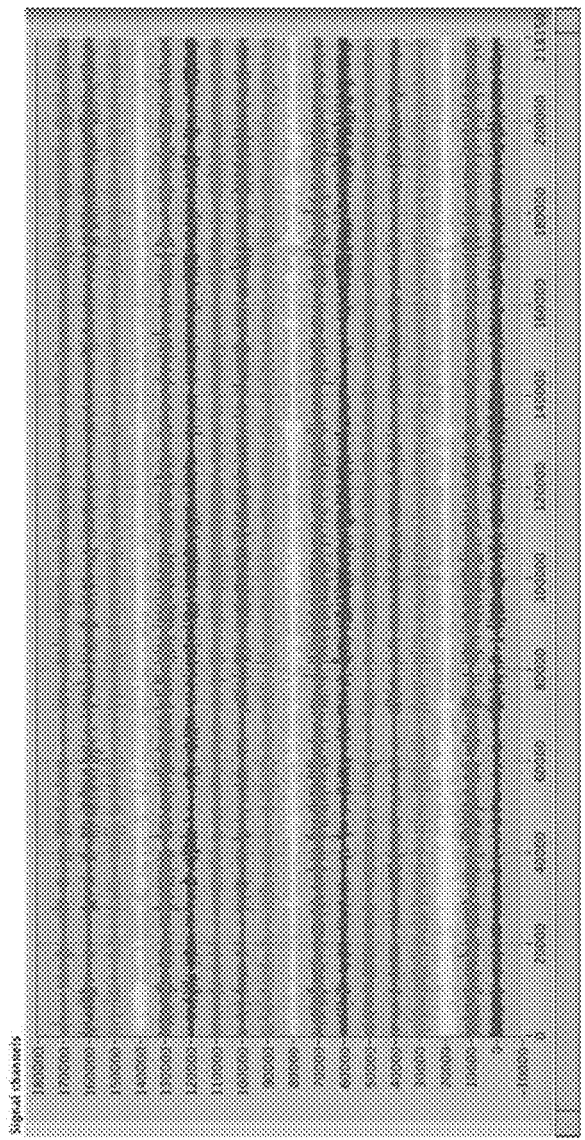
FIG. 27 shows a data set from Subject 012 after data normalization.

FIGS. 22-27 show time series data on 18 channels from electrodes placed in a matrix on the abdomen of three subjects, representing 3 hours of data at 20 Hz. The data, as shown, are filtered outside of the rang 0.5 to 25 cpm (cycles per minute). FIGS. 22, 24 and 26, show data from the 3 subjects before normalization; FIGS. 23, 25 and 27 show the same data from each of the subjects, respectively, after normalization, using the range from 25 to 45 cpm to determine the normalization factor. Although the amplitudes of the signals in FIGS. 22, 24 and 26, are quite different form one another, after normalization, the data in FIGS. 23, 25 and 27 are much more similar to each other. Spectral quantities based on the data sets, such as the height of peaks and the baselines between peaks, are much more consistent after normalization. The values of the multiplicative normalization factors in these examples are 2.10, 1.45 and 0.53, respectively.

Figure 28:
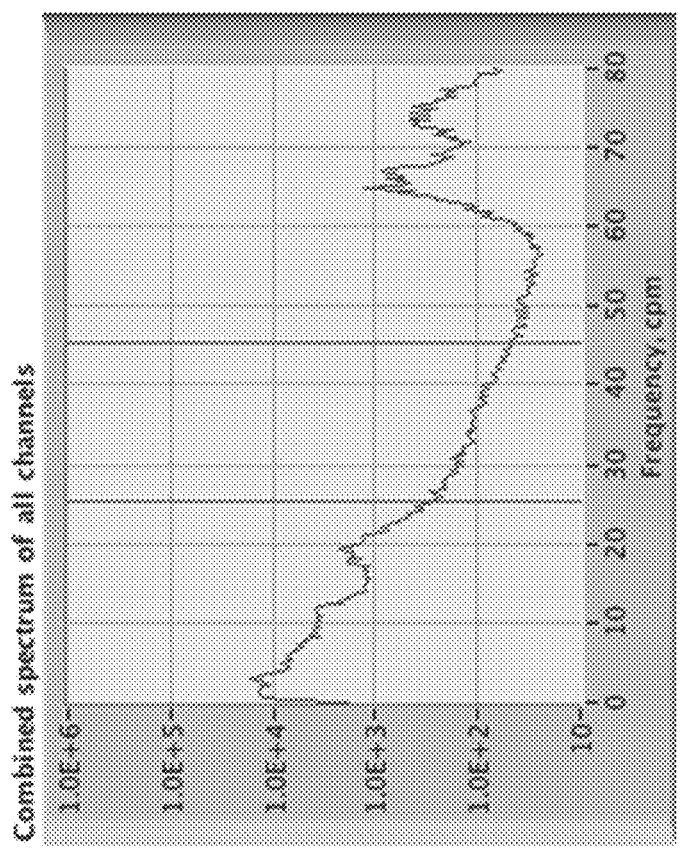
FIG. 28 shows spectra of all channels showing quiet region from 25 to 45 cycles/min (cpm) flanked by structures on either side.

In the examples shown in FIGS. 22-27, the normalization factor was determined by integration of the spectrum of each channel of data over the range 25 to 45 cpm, divided by a standard value that was the mean of a set of such measurements, followed by a square root operation. The range chosen for this example has a generally uneventful spectrum, carrying a certain amount of random nose, but above the signals of interest from the gastrointestinal tract and below those typically seen from the heartbeat. A spectrum example is shown in FIG. 28 where the red cursors indicate the region of interest (ROI). Without such signals confounding the data, this region is appropriate for determining the degree of electrical coupling of the electrodes through the skin and tissues to the internal organs.

Figure 29:
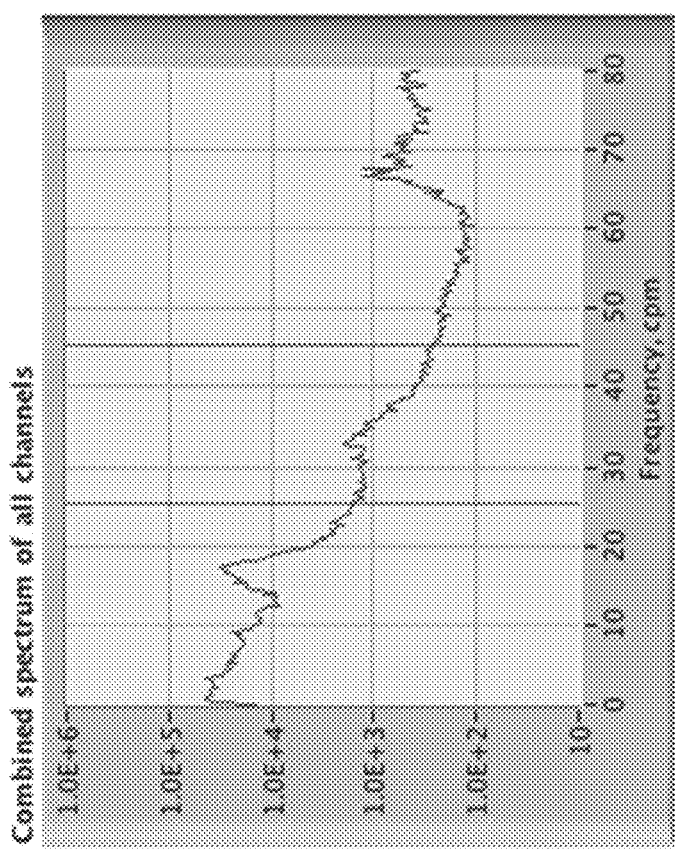
FIG. 29 shows a spectrum with a peak in the 25 to 45 cpm region from harmonies of the 16 cpm primary peak.
Figure 30:
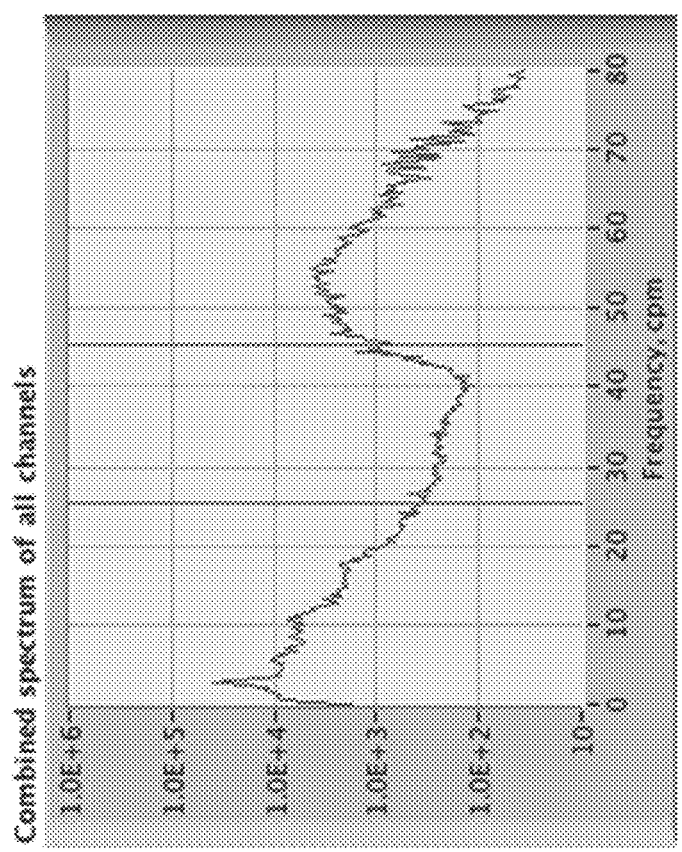
FIG. 30 shows a spectrum with energy in the 25 to 45 cpm region from the lower edge of the heartbeat peak.

However, it is not always the case that the aforementioned or any other predetermined range will be free of these subject-dependent structures. FIGS. 29-30 show an example where a harmonic of the 16 cpm peak adds energy to the region, and where the patient's heart beat is unusually low for part of the test and does the same. Since these structures are specifically dependent on the patient and add energy to the spectrum, they bias the normalization factor and introduce inaccuracies in any parameter derived from a comparison between this patient's results and that of others, such as a percentile ranking of activity.

In order to determine the most accurate normalization factors it would be valuable (advantageous to) to avoid the types of structures shown in FIGS. 29 and 30 when identifying a region of data as a quiet data region. While the eye and brain together provide a powerful tool for achieving this result, it is desirable to have the process automated by a computer algorithm. One such approach involves determining a local slope parameter, essentially a derivative but filtered to remove high frequency components. Note that in FIG. 28 the spectrum in the sample's region of interest, or portion thereof, has a simple and well defined behavior, in this case a downward slope with some gentle upward curvature.

It is possible to define a range of slope values that represent "quiet" behavior over a region of interest, and to sue this range to specify the limits of a region of interest for use in normalization. Further it is possible to additionally use the curvature as determined by the second derivative as additional criteria. One method of doing so involves specifying a range of derivative and second derivative values and selecting a contiguous region that meets the criteria, the region being chosen from a larger region that is known to be a good candidate region, i.e. avoiding the frequencies where peaks of interest are known to appear, for example the larger region might be the 25 to 45 cpm shown in the examples, but could also be a larger or smaller region, or one entirely different.

A more sophisticated method for selecting the region of interest involves using a range of acceptable slope and second derivative values defined on a local basis that would be narrower. For example, the ranges could be defined for each cycles/minute (cpm) value based on expected behavior calculated from a set of measurements that were visually identified as being acceptable and appropriate. This approach has the benefit of being more precise, and is easily performed by computer algorithm.

Figure 31:
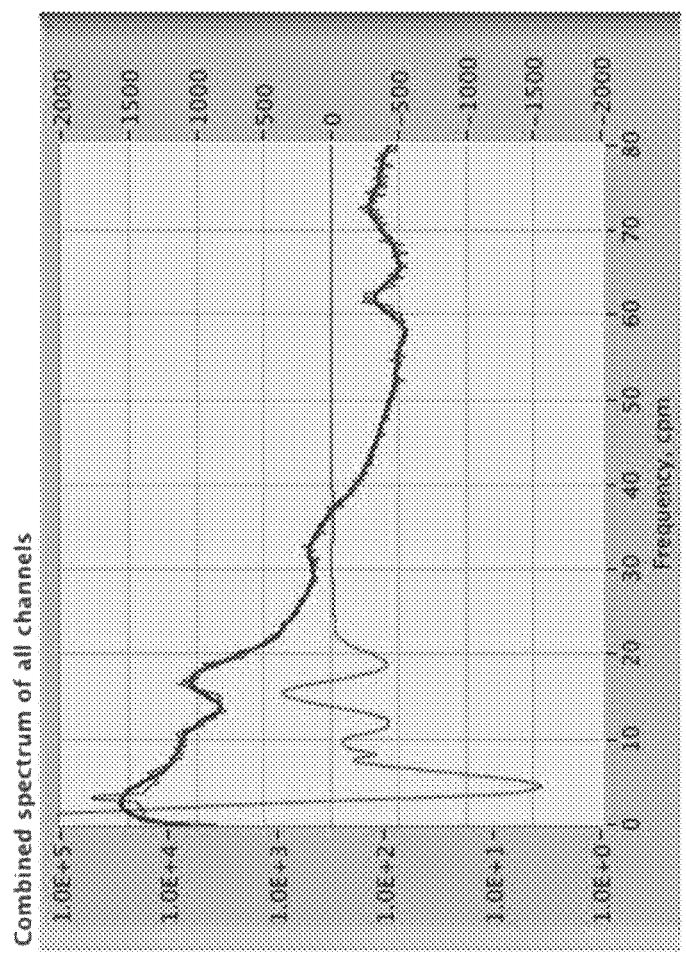
FIG. 31 shows a spectrum in blue and derivative in red.
Figure 32:
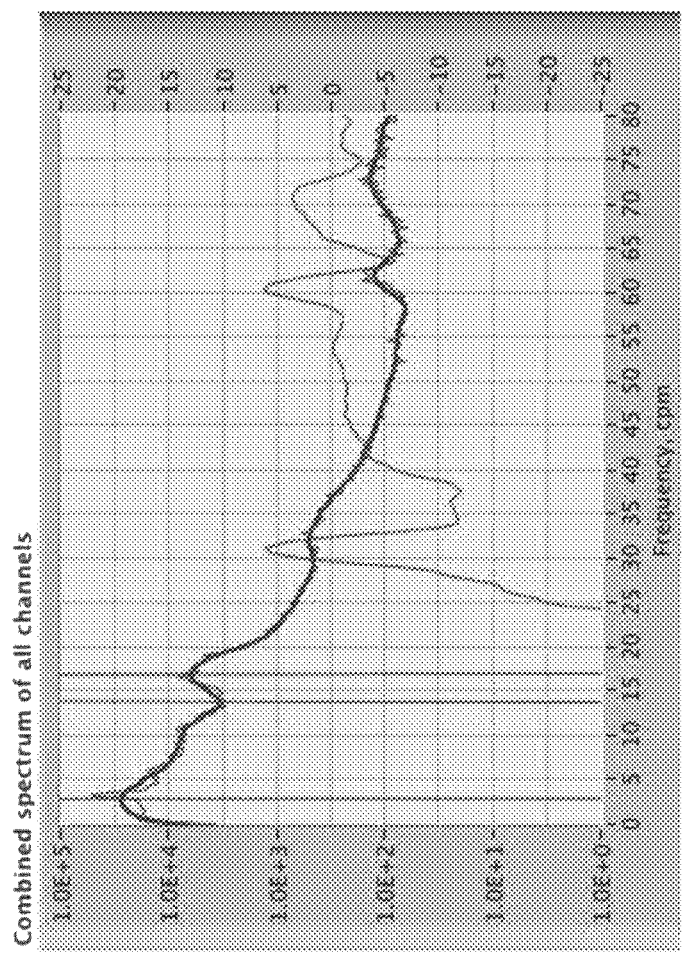
FIG. 32 shows a spectrum in blue and derivative in red.

FIG. 31 shows a spectrum with a smoothed version superimposed thereon, and the derivative of the smoothed version. The spectrum is linked to the logarithmic scale on the left while the derivative uses the linear scale on the right. In this example, there is a small bump in the spectrum centered about 33 cpm that is not desirable for inclusion. The derivative in this plot is close to zero the region 25 to 45 cpm, but only because the scale was chosen to show the entire extent. In FIG. 32, the vertical range is zoomed in and one can see that there is significant structure in the derivative in that region. In particular, the aforementioned bump produces a substantial positive and then negative going excursion in the derivative front 30 to 40 cpm. Conversely the region from 40 to 55 cpm that is quiet in the spectrum has a derivative that is within −5 to 0. Thus it cat be seen that the derivative is a useful means of determining a region of interest that has the quietness characteristics desired in a normalization region.

Figure 33:
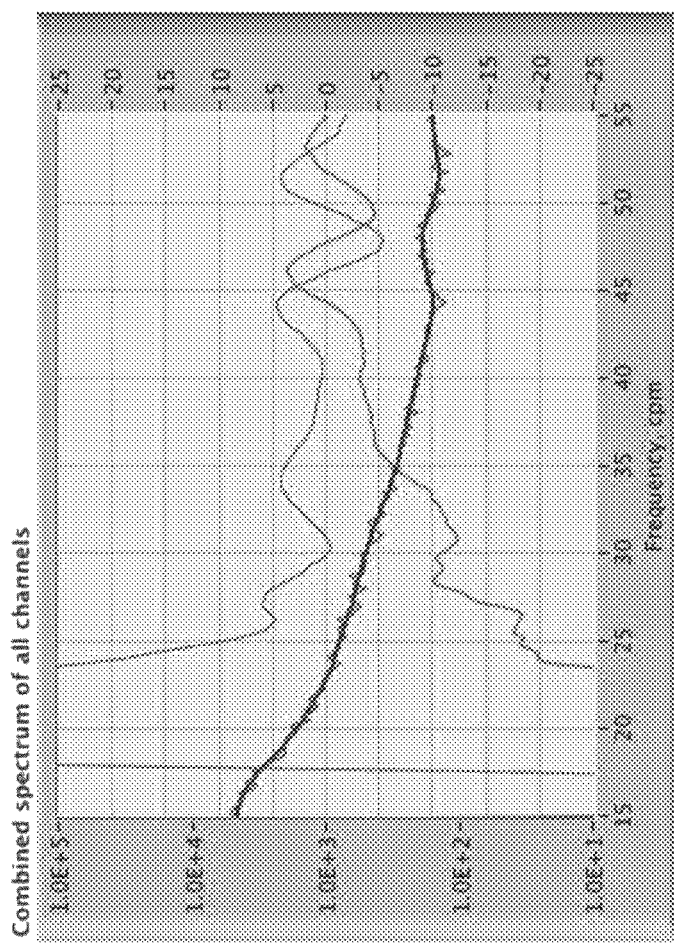
FIG. 33 shows a spectrum in blue, derivative in red, and second derivative ×10 in green.

FIG. 33 shows a data set that has the desired quietness characteristics in the region of interest from 25 to 45 cpm and which is representative of many other sets in terms of the general shape of the spectrum in the region. The derivative shown in red is within the range −20 to +2 while the second derivative shown in green is within the range 0 to 10. In the region of interest 35 to 45, the derivative is similar to the previous set of figures in that it is within −5 to 0, but from 25 to 35 cpm, the range is wider. This illustrates the value of creating a set of acceptable ranges that are local in the sense specified earlier, that is, apply only to a specific subset of the region of interest, based on known characteristics of data that is identified as acceptable. The algorithm effectively uses the information gleaned by human insight on a relatively small set of samples to apply in a uniform, automated way to large numbers of data sets.

The technique outlined allows a computer algorithm to select a region of interest that is appropriate for use in normalization of the data set the spectrum comes from. However as can easily be seen in the figures, if one selects a region of interest at lower frequencies the integrated value will necessarily be higher than if the region of interest is predominantly at higher frequencies, and it will be less if the region is small than if the region is large. Thus the normalization factor must take into account both the width of the region of interest selected, and the specific frequencies. This can be accomplished by mathematically modeling the expected or nominal spectrum and calculating the normalization factor in comparison only to the same section of the nominal spectrum.

Characterization

A traditional approach when dealing with such large datasets with characteristics that contain repetitive or rhythmic signals is to summarize it in terms of its frequency parameters, through Fourier transforms and specifically a power series spectrum. Time is not necessarily eliminated from the analysis, nor is it desirable to do so, by use of the spectral approach as the spectra can be calculated in blocks over time.

There is a great deal of clinically useful information in the time dependent spectra, but extracting this information is challenging due to a number of factors, including (1) its vastness, (2) the presence of substantial noise relative to steady state levels and signal peaks, (3) the fact that the natural frequencies are very low and in many cases do not last for a large number of cycles, (4) the presence of multiple channels of data rather than just one, and (5) the interpretation of the levels and peak data patterns or structures as physiological markers.

This disclosure provides a novel approach to identifying the spectral peaks that occur due to rhythmic muscle activity in and around the gastrointestinal tract, determining the key characteristics of peak frequency, height, width and duration, and assigning the discovered peaks to specific sources. Some of the challenges facing peak detection and quantification will now be enumerated.

Peak detection by an automated approach is of interest in many fields, each with their own set of challenges depending on the nature of the input data and the desired output. When the data have a high signal-to-noise ratio with a steady baseline and large peaks relative to the baseline, it can be easy to identify the location of peaks by simply setting a threshold value, and assuming that any data points above the threshold represent a peak or a portion thereof. However, even in this simplest of cases one must then identify the contiguous points that make up each peak, determine whether the peak center is the central point, the highest point, or some combination determined, by, for example, applying filtering to the data. If one also wishes to determine the intrinsic height of the peak, and/or its width at half max, more work needs to be done and more choices are faced, for example with the type of filter to be applied to the data and the filter settings. If one also needs the area of the peak then the background level must be estimated, and the beginning and end points of the peak at its base, again leading to more algorithmic complexity and more choices.

When the data are very noisy and the peaks, when present, are not significantly higher than the background, detecting a peak becomes very challenging. If the background level varies substantially within a data set or even between data sets, more complexity is introduced. Measuring the parameters of the peaks becomes yet more challenging, and algorithms that attempt to do so must deal with many confounding situations. The frequency spectra of surface detected gastrointestinal myoelectric data are an example of a difficult situation for detecting and characterizing peaks.

When one is interested in the evolution over time or spectral peaks, for example to determine the start time and duration, and where the time scales are short relative to the frequencies involved such that there may be only tens of cycles or fewer of the rhythmic behavior that is under scrutiny, yet more complexity is involved and more choices arise. The obvious way of dealing with transient peaks is to break the data into time segments (with or without windowing and/or overlap). When the time segments are short, one has the best time resolution on determining the start time and duration, but if a large number of cycles is not contained in the time segment, the resolution suffers, and the signal-to-noise ratio is lower than it would be for a longer time segment with more cycles.

Figure 34:
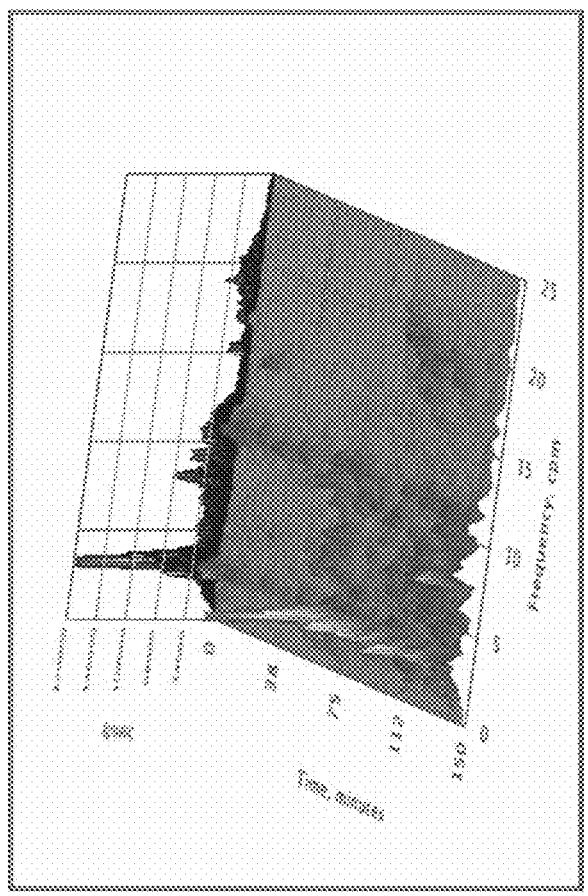
FIG. 34 shows a pseudo-3D "waterfall plot" of spectra taken from a 2.5 hours long data set, with time segments of 4 minutes.
Figure 35:
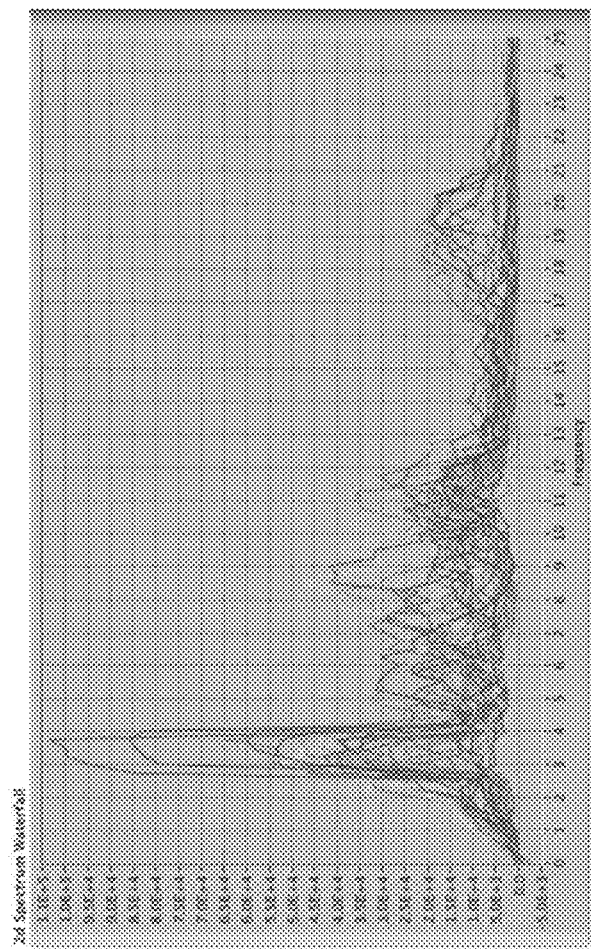
FIG. 35 shows the same data as those shown in FIG. 4 as a series of line plots rather than a pseudo-3D plot.

FIG. 34 shows a pseudo-3D "waterfall plot" of spectra taken from a 2.5 hour long data set, with time segments of 4 minutes. Time runs from rear to front in minutes while frequency runs from left to right in cycles per minute (cpm). Rhythmic behavior, representing periodic contractions of the smooth muscles in the walls of the digestive organs leads to peaks in the spectra. Peaks in FIG. 34 are quite clear to the eye for extended times at 3 to 10 cpm, and intermittently at several other frequencies. The peaks at 3 cpm are quite narrow and tall while those at the other frequencies are mostly broader and of lower amplitude on this scale. Any algorithm for peak detection based on a fixed threshold would either detect only the tallest peaks, or else would be subject to a great deal of noise if the thresholds were low enough to detect all of the peaks. This should be clear from FIG. 35, which shows the same data as a series of line plots rather than pseudo-3D plot.

An improvement over the single value threshold, which is effective when there are multiple sets of data involved whether from multiple channels or multiple patients, is to use a threshold value that adapts to the data itself. One approach is to set a threshold based on a percentile ranking of all points in the set, for example at the 90th percentile. Other approaches in the same spirit can be employed as well, for example using a value set at 90% of the largest data point. This approach can be further improved by breaking the frequency range into several sub-ranges, and treating each sub-range separately, so that peaks that are larger in one sub-range do not eliminate the possibility of detecting peaks in other sub-ranges. One way of choosing sub-ranges is to select ones that represent the expected ranges for stomach, small intestine, and colon, approximately 2 to 4, 5 to 12, and 12 to 25 cpm respectively. Alternatively, one can choose sub-ranges that individually surround each of the peaks previously observed. Since peaks can show up at different places for different patients, the sub-ranges can be allowed to overlap. Depending on the subsequent processing of the detected peaks, such overlap will need to be taken into account, say to avoid double counting of a peak on the border between two sub-ranges.

Figure 36:
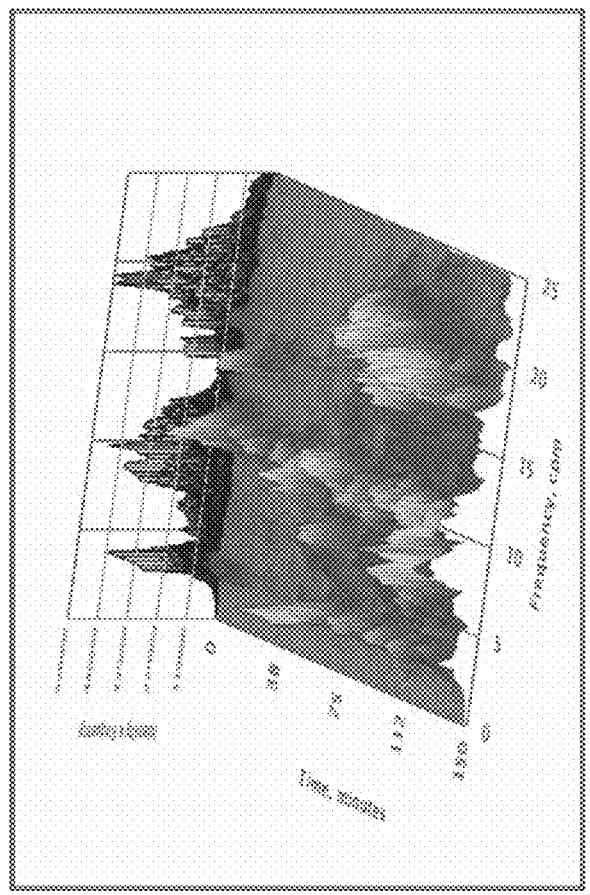
FIG. 36 shows the same data as in FIG. 4 but with frequency weighting applied.

Another way of adjusting to the fact that there can be peaks at different heights even in a sub-range, takes account of the fact that the amplitude of signals (peaks and background) in general tends to drop with frequency. To compensate for this, one can weight the spectrum by the frequency. FIG. 36 shows the same data as in FIG. 34 but with frequency weighting applied. It can be seen that the peaks in this case are now all of similar amplitude, which can ease the task of determining a peak threshold.

In determining the height and area of a peak, it is necessary to account for the level of background, i.e., the amplitude that would obtain if the peak were not present. If this is not taken into account, and the peak is considered to start at an amplitude of zero, a bias will be introduced when comparing peaks. By way of an example, consider a first peak with amplitude 1 unit, and a second peak with amplitude 2 units, both on a background of 1 unit. The actual ratio of peak 2 to peak 1 is 2, but if the background is not taken into account the calculated ratio will be 3/2.

As with detecting peaks, determining the background level is something that is easy to do by eye, but much more challenging to do well by way of an automated algorithm. If the peaks are isolated, with large gaps between them, there are a number of approaches that can be employed such as averaging a set of pints from the middle area between peaks, on either side of every peak, and using the average of the two sides. When the peaks are less clearly delineated, or when the background information is needed as part of the peak identification algorithm, a different approach is required. In the method provided herein, the background is estimated a priori by a mechanism analogous to that used in setting the peak threshold. A percentile rank value or percentage of range value is used as the background, the value being informed by analysis of previous data sets, and set on a sub-range specific basis, and depending on whether the spectrum is frequency weighted or not.

Having set peak detection thresholds, one can begin to identify valid peaks simply by noting what points exceed the threshold. One can also employ standard algorithms that provide additional discriminatory value such as those included in software packages such as LabVIEW or Matlab. If using such algorithms, it is necessary to provide setpoints that control the discriminants, and these can be incorporated into the full set of sub-range setpoints.

With the type of data found in myoelectric measurements of gastrointestinal motor activity, the peaks when present are often not much higher than background and not much greater than the typical noise level, yet it is desirable to identify and characterize all peaks. As a result of the low signal-to-noise ratio, the standard algorithms often return results that are driven by noise rather than by real peaks, and additional discrimination is needed to separate the valid signals from the noise. One can apply filtering to reduce the noise, but this tends to smear peaks and reduce their height, and therefore must be done in moderation, and to be optimal should be done on a sub-range specific basis as well.

Figure 37:
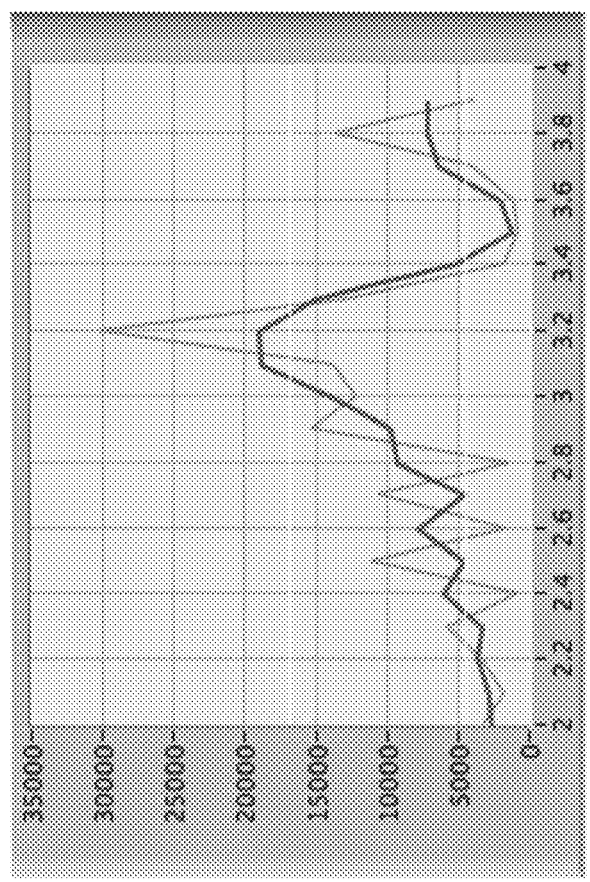
FIG. 37 shows a spectrum containing a single peak (in red) over a sub-range from 2 to 4 cpm, with filtered version in blue and cursors showing background level and peak threshold.

FIG. 37 shows a spectrum front a 4-minute time segment from the sub-range 2 to 4 cycles/min (cpm) with a relatively clear peak. From our empirical observations, in this frequency range, one peak from physiological sources can be expected, at most. The calculated spectrum is in red and a filtered version in blue. Horizontal yellow lines indicate the background level at about 5,000 units and the peak threshold at 17,000, both calculated based on the filtered values. This example shows that even when there are clear peaks the analysis benefits from filtering and a threshold that reflects the data itself rather than a predetermined absolute value.

Figure 38:
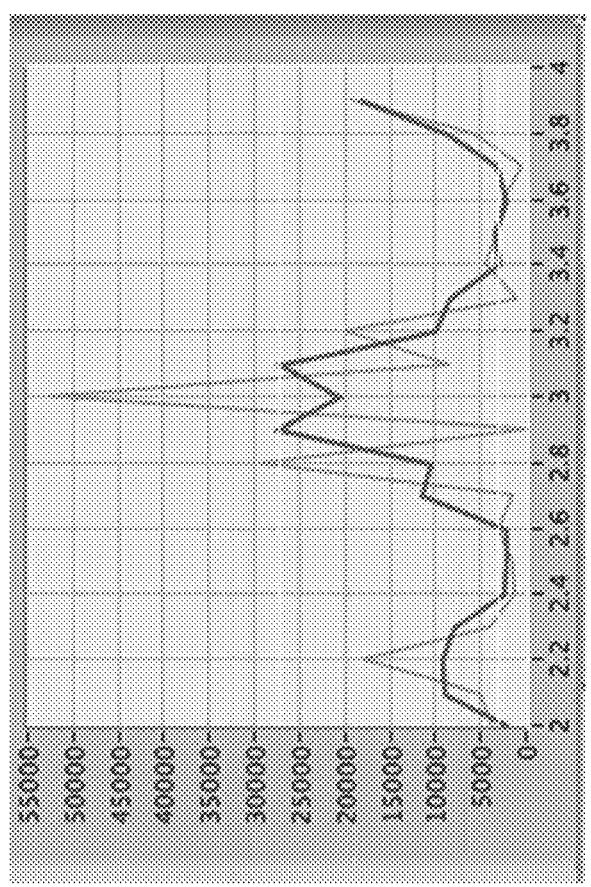
FIG. 38 shows a noisy spectrum leading to identification of 3 peaks.
Figure 39:
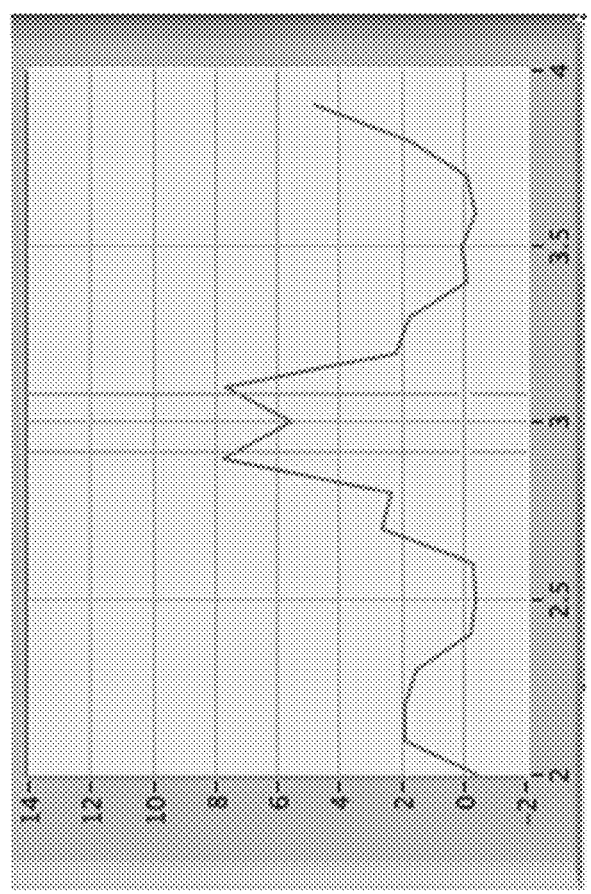
FIG. 39 show's the location of peaks identified in first phase of processing from FIG. 9 in net scaled amplitude data.

FIG. 38 is more complicated application of the described method; the data are very noisy, and although filtering reduces the variation, there are still multiple peaks above the threshold, in this case at 25,000 units. The identified peaks are shown in FIG. 39. A slightly higher threshold would lead to a single peak in this case, but in a large dataset such data complexity is common, and so the automated algorithm must have a mechanism to deal with it.

Therefore, as provided herein, a second phase of processing sets criteria for what is a valid peak and what is not, based on an approach that imposes "cuts" based on both numeric and logical values. Imposing cuts is intended as a general post-peak-identification process, not to be limited to the examples that follow. Use of cuts follows a straightforward process that makes it inherently extensible. Starting with the broad set of all candidate peaks initially identified, the cuts are imposed one by one, eliminating those candidates that do not meet the chosen criteria. The cut criteria can be either quantitative or logical (yes/no).

To illustrate the concept of cuts. FIG. 39 shows two candidate peaks identified by the first part of the automated algorithm that appear quite close together and can be reasonably assumed to be a single peak. The cut used to eliminate this behavior tests the separation between peaks against a setpoint value. If the peaks are further apart than the setpoint, they both are passed to the next test; but if they are closer than the setpoint, they are combined into a single peak, at a frequency determined either by a simple average or with an average weighted by the amplitude of each.

A second example of a cut concerns the degree to which the peak is isolated, and requires the amplitude on either side to drop to a fraction of the peak height, typically one half but not necessarily so. Typically but not exclusively the values examined would be net values, that is, with the background subtracted.

A further example of a cut concerns the amplitude of the candidate peak. This can be applied in multiple ways, ensuring that there is a minimum value of absolute amplitude, net amplitude and/or scaled amplitude, where sealed amplitude is net amplitude divided by background thereby representing multiples of the background level.

A yet further example concerns peaks near the edge of the sub-range, where it can be required that the peak center, or half-max location, or similar parameter be at least a minimum distance from the edge.

Additional cuts can easily be imagined depending on the specific goal of the analysis, for example demanding there be only one peak, or that it be within a particular frequency range or amplitude range, or have a slope on either side within a specified range, and so forth.

The total amount of energy in a peak emanating from motor activity in a gastrointestinal organ over its duration is of interest in understanding the operation of the digestive system as it relates to motility events in the organ. To measure this total energy the total volume of the peak, height times width times duration, is calculated. Duration is thus an additional parameter that needs to be extracted from the spectrum. The inherent challenge in doing so for gastrointestinal myoelectric data concerns the fact that the waves are slow, as slow as 2 cycles per minute. When calculating a spectrum, the peak width depends on the number of cycles of activity included in the time series data. The fewer the cycles, the broader and shorter the peak, resulting in poorer resolution.

Figure 40:
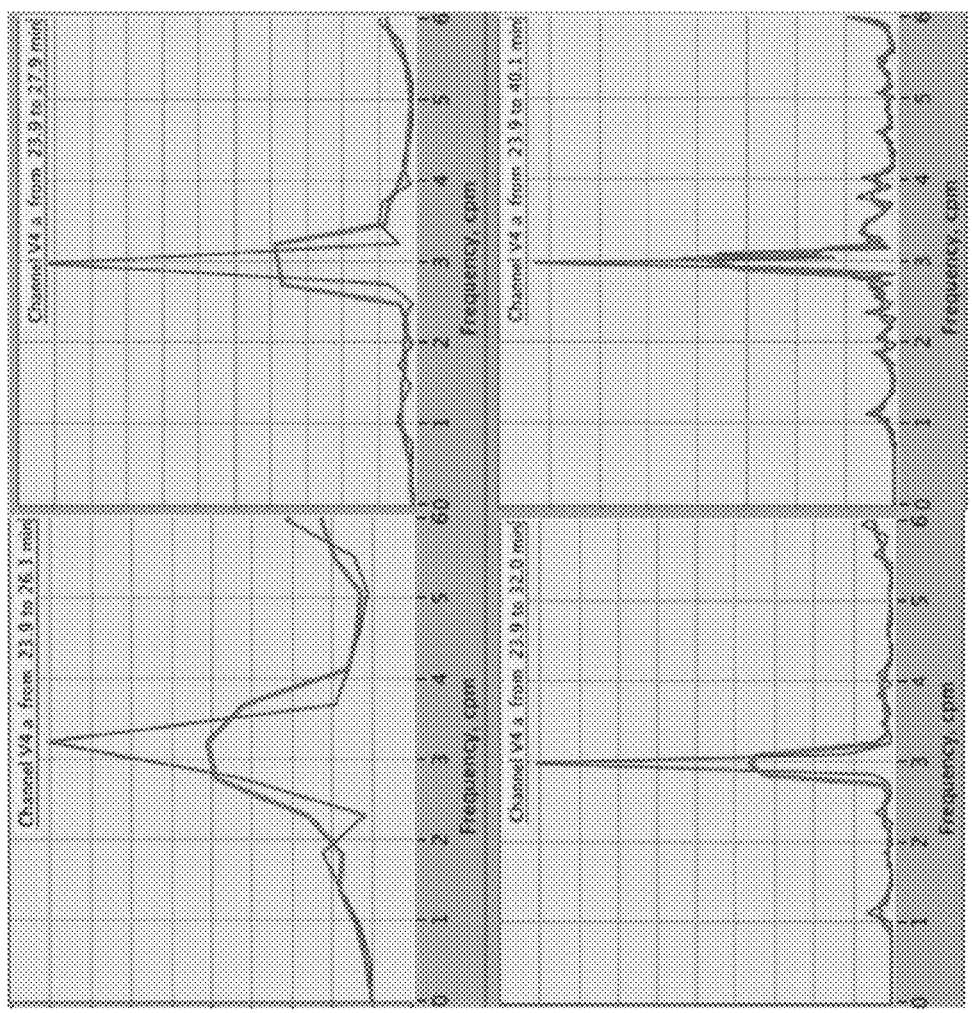
FIG. 40 shows spectral peaks from stomach motor activity at 3 cycles/min (cpm), using time segment lengths of 2, 4, 8 and 16 minutes, illustrating the increased resolution obtained with longer time periods. The blue line represents the raw spectrum; the red line is a version with Savitsky-Golay smoothing of rank 1 applied.

FIG. 40 is an example of a spectral peak using 2, 4, 8, and 16 minutes of data, illustrating how the resolution improves with longer time periods of data collection. Therefore it is desirable to use longer time segments in the spectral analysis to obtain narrow tall peaks that can easily be identified. Unfortunately, the use of longer time segments to improve frequency resolution lowers the resolution in the time dimension. Longer time segments can also lead to a broader measured peak if the actual peak frequency is changing during the time period, as is known to occur with some of the gastrointestinal signals. It is thus advantageous to use an optimum time segment in trading off resolution in frequency vs. resolution in time.

To determine the peak start and end times, and thereby duration, one needs to identify the edges of the peak in the time dimension, analogously to what is done in the frequency dimension, for example, by finding the point at half-max above background at the leading and falling edges of the peak. An alternative approach, if what one is interested in is the total volume of the peak, is to ignore the rise and fall points and simply calculate the volume from beginning to end of the time segment using the height, full width and half maximum, and segment duration. The process of calculating the spectrum integrates over the length of the time segment, so a brief peak will simply show up as a smaller peak, and as along as it is detected, there will be no bias introduced by using the time segment length as the peak's duration.

As an approach to improving the ability to detect and measure the parameters of frequency peaks, an aspect of the current disclosure involves setting the time segment lengths adaptively. This can be accomplished by processing the data multiple times with different time segments, say 1, 2, 4, 8 and 16 minutes long, and then examining the peaks found to narrow down the likely start and end times, and further performing an analysis using a set of time segments that are based on the determined start and end times. Peaks can first be identified in any time segment, but the longer ones, in particular, have better signal-to-noise ratio for longer lasting peaks, and then the shorter time segments can be examined at the frequency of the found peak to determine when they begin and end. If the peak location is known, the selection criteria can be relaxed in the shorter time segments, using the rationale that it is easier to find something if you know that it is present.

Another approach is to use sliding time segments. The use and value of this can be understood by way of the following example. If there is a peak of duration 4 minutes and the chosen time segment length is 4 minutes, a high signal-to-noise ratio can be achieved if the time segment is synchronized with the peak's existence. However, in general, this will not be the case. Using a 4-minute segment and shifting so that it re-starts every minute allows for the algorithm to find the best setting with highest signal-to-noise ratio. This approach can be combined with the approach (previously noted) that identifies the start and end times of each peak, and then sets time segments exactly around those times, to obtain optimum signal-to-noise ratio.

Having identified a set of peaks and determined their parameters of frequency, height, width, and duration, one can calculate the volume of each peak which can then be used as a measure of motor activity in the relevant organ. As there will be multiple peaks coming and going over time, and at different frequencies, as well as over multiple channels of data, it is desirable to combine the volumes in some way to summarize the results in a smaller number of metrics. Further it is desirable to combine them in a way that reflects the frequency of the activity, as this is of physiological interest. The challenge of doing so is that the measured frequencies are not always tightly grouped and widely separated.

Figures 41A, 41B:
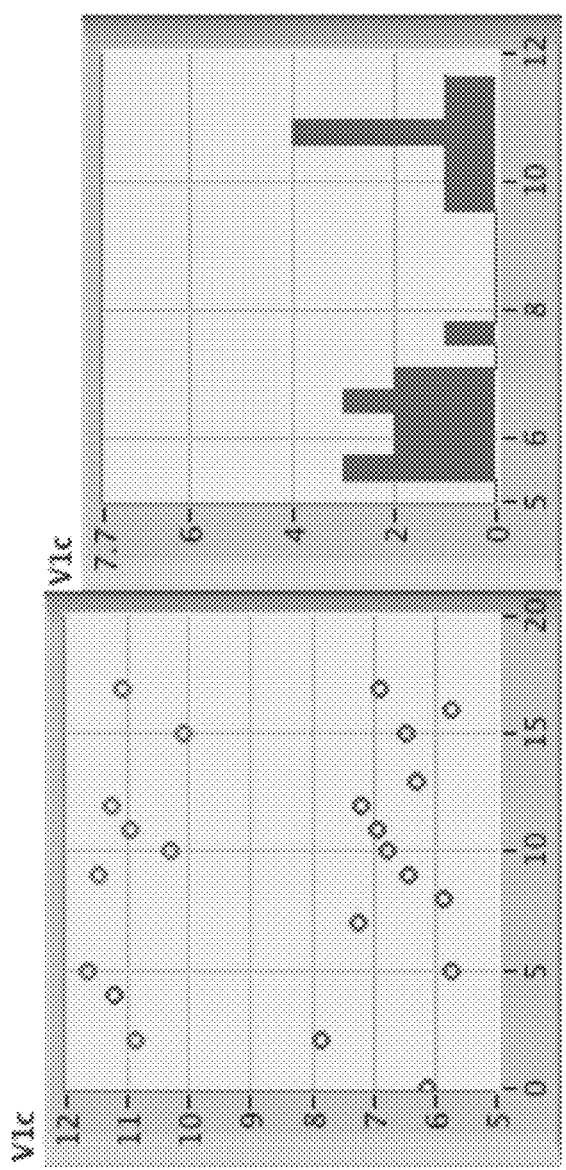
FIG. 41A shows data from time segments of 10 minutes and peak frequencies detected over time in 10 minutes.
FIG. 41B shows data from time segments of 10 minutes.

FIG. 41A shows the frequencies detected per time segment and FIG. 41B shows their distribution in histogram form. In FIG. 41A, blue circles show the first peak detected while red indicates that a second peak has been detected in that time segment. The identified peak frequencies can be seen to form groups at around 6 and 11 cpm. Just as peak detection was used to determine the location and frequency of peak in the spectra, peak detection can be used to find the location of significant groupings when the frequencies of detected peaks are made into a histogram. By so doing, peak groups can be identified, and individual peaks can be assigned to one group or another based on criteria such as which value they are closest to. Once groupings are assigned, total peak volumes can be calculated by adding all the volumes from each peak in the group.

Any one or more features of any embodiment disclosed herein can be combined with any one or more other features of any other embodiment, without departing from the scope of the present invention. Further, although the present inventions have been disclosed in the context of certain preferred embodiments and examples, it will be understood by those skilled in the art that the present inventions extend beyond the specifically disclosed embodiments to other alternative embodiments and/or uses and obvious modifications and equivalents thereof. Thus, it is intended that the scope of the present inventions herein disclosed should not be limited by the particular disclosed embodiments described above, but should be determined only by a fair reading of the claims that follow.

The systems and method and variations thereof can be embodied and/or implemented at least in part as a machine configured to receive a computer-readable medium storing computer-readable instructions. The instructions are preferably executed by computer-executable components preferably integrated with the system and one or more portions of the processor. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "peak" may include, and is contemplated to include, a plurality of peaks. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicated approximations which may vary by (+) or (−) 5%, 1% or 0.1%. All numerical ranges provided herein are inclusive of the stated start and end numbers. The term "substantially" indicates mostly (i.e., greater than 50%) or essentially all of the device, substance, or composition.

As used here, the term "comprising" or "comprises" is intended to mean that the devices, systems, and methods include the recited elements, and may additionally include any other elements. "Consisting essentially of" shall mean that she devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of extracting valid gastrointestinal tract EMG data from a raw time series data set acquired from a skin-surface mounted electrode patch, the method comprising:

obtaining data from one or more skin-surface mounted electrode patches, wherein each patch comprises two or more bipolar pairs of electrodes arranged substantially orthogonally forming an array of bipolar pairs of electrodes configured to sense and acquire EMG voltage signals such that each bipolar pair of electrodes of the array of bipolar pairs of electrodes corresponds to a single channel of raw time series data, examining the distribution of signal across the bipolar pairs of electrodes, wherein the orthogonal arrangement of the bipolar electrode arrays are configured to provide spatial information about the relative placement of the electrodes such that the pattern of amplitudes across the channels indicates whether a signal in a given channel should be included in a valid gastrointestinal tract EMG signal;

identifying artifacts within the raw time series data across the array of bipolar pairs of electrodes, said identifiable artifacts comprising a set of data points nominally centered on a point of largest excursion from average value of zero-crossing and extending toward the average or zero-crossing for each bipolar pair of electrodes in each channel corresponding to each bipolar pair of electrodes;

eliminating the identified artifacts by tracking them down to any of a zero-crossing or a midpoint-crossing point on either side of a high amplitude artifact; and replacing the artifacts with any of interpolated points or constant value points that span a gap across the eliminated artifacts to create a clean time series data set comprising the valid gastrointestinal tract EMG signals.

2. The method of claim 1, wherein identifying artifacts is based on the standard deviation of a set of points in the data set.

3. The method of claim 1, wherein identifying artifacts is based on a percentile ranking of a set of points where the artifact is identified is a structure having at least one data point in an extreme percentile.

4. The method of claim 1, wherein identifying artifacts comprises filtering the raw time series data to remove low frequencies or high frequencies from each channel.

5. The method of claim 1, wherein identifying artifacts comprises offsetting data amplitude by an average amplitude, thereby creating a data set with an average value of zero.

6. The method of claim 1, wherein identifying artifacts comprises tracking to the nearest zero-crossing or midpoint-crossing, the individual point nearest to zero/midpoint is selected on either side, and replacement points are interpolated between the two points so determined.

7. The method of claim 1, wherein identifying artifacts comprises tracking to the nearest zero-crossing or midpoint-crossing, and all replacement points are set to zero or to the midpoint value as appropriate.

8. The method of claim 1 wherein replacing artifacts comprises smoothing of values on either or both sides of the gap between eliminated artifacts to minimize spectral effects from an abrupt edge transition.

9. The method of claim 1, wherein replacing the artifacts further comprises recording any of the number of replaced data points or the amount of elapsed time associated with them to allow any further data processing to compensate for the absence of data.

10. The method of claim 1, wherein identifying artifacts comprises using a predetermined threshold criterion.

11. The method of claim 10, wherein using a predetermined threshold criterion is applied in a repetitive manner.

12. The method of claim 1, wherein identifying artifacts comprises using an adaptive threshold criterion, such adaptive threshold criterion based on statistical measures complementary to a statistical measure used to set a preliminary threshold.

13. The method of claim 1, wherein identifying artifacts comprises using characteristics of data shape that have been previously identified as artifactual.

14. The method of claim 13, wherein the data shape includes a rapid initial excursion followed by an approximately exponential decay with or without subsequent ringing.

15. The method of claim 1, wherein identifying artifacts comprises evaluating a power spectrum from all or a section of the time series data set and determining that a particular region of the time series data set is heavily burdened by artifacts based on a shape of the power spectrum.

16. The method of claim 1, wherein a time series event in raw time series data coincidentally occurs on a plurality of channels comprising raw time series data from each bipolar electrode pair, wherein such coincidence occurrence is considered indicative that the time series event is an artifact.

17. The method of claim 1, wherein artifacts that have the characteristics of an analog-to-digital converter (ADC) error are replaced by data points interpolated between the unaffected points on either side.

18. The method of claim 17, further comprising filtering the raw data to remove low frequencies or high frequencies.

19. The method of claim 1, further comprising segregating the raw time series data set into sub-regions, the method steps then being applied to each sub-region independently.

20. The method of claim 1, further comprising
modifying the raw time series data set to create a modified time series data set wherein identifying the artifact occurs within the modified time series data.

21. The method of claim 1, wherein the signal is included in the valid gastrointestinal tract EMG signal if the amplitudes of each channel drop off gradually in all directions across the patch or patches, and the signal is eliminated if the amplitudes of each channel do not decrease in accordance with the detected spatial arrangement of the bipolar electrode pairs for the data from each of the corresponding channels.

22. The method of claim 1, wherein the patch comprises two to ten embedded bipolar pair electrodes with an inter-electrode distance of between 0.5 and 3 inches configured to collect a gastrointestinal tract EMG signal and generate a clean time series data set with a valid gastrointestinal EMG signal comprising slow wave signals obtained from skin-surface mounted electrode patches disposed from the abdominal region of a patient, wherein the valid gastrointestinal tract EMG signal is in the range of 1 to 30 cycles per minute obtained from raw time series data collected continuously over a period of greater than or equal to two days.

* * * * *